United States Patent
Watanabe et al.

(10) Patent No.: US 12,429,454 B2
(45) Date of Patent: Sep. 30, 2025

(54) GAS SENSOR

(71) Applicant: NGK INSULATORS, LTD., Aichi (JP)

(72) Inventors: Yusuke Watanabe, Nagoya (JP);
Shotaro Niizuma, Kasugai (JP);
Toshihiro Hirakawa, Kasugai (JP);
Hayami Aota, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 115 days.

(21) Appl. No.: 17/497,014

(22) Filed: Oct. 8, 2021

(65) Prior Publication Data
US 2022/0113279 A1 Apr. 14, 2022

(30) Foreign Application Priority Data
Oct. 12, 2020 (JP) .................................. 2020-171670

(51) Int. Cl.
*G01N 27/41* (2006.01)
*G01N 27/407* (2006.01)
*G01N 33/00* (2006.01)

(52) U.S. Cl.
CPC .......... *G01N 27/41* (2013.01); *G01N 27/4071* (2013.01); *G01N 33/0037* (2013.01)

(58) Field of Classification Search
CPC .............. G01N 27/41; G01N 27/4071; G01N 33/0037; G01N 27/4072; G01N 27/419; Y02A 50/20
See application file for complete search history.

(56) References Cited

U.S. PATENT DOCUMENTS

| | | | | |
|---|---|---|---|---|
| 2003/0062904 | A1* | 4/2003 | Katafuchi | G01N 33/0037 324/439 |
| 2008/0105545 | A1* | 5/2008 | Nakagaki | G01N 27/419 204/424 |
| 2012/0255356 | A1* | 10/2012 | Kume | F01N 13/008 73/431 |

(Continued)

FOREIGN PATENT DOCUMENTS

| | | |
|---|---|---|
| JP | 2004-151018 A | 5/2004 |
| JP | 2006-170888 A | 6/2006 |

(Continued)

OTHER PUBLICATIONS

Unexamined U.S. Appl. No. 17/497,012, filed Oct. 8, 2021.
Unexamined U.S. Appl. No. 17/497,016, filed Oct. 8, 2021.

*Primary Examiner* — Luan V Van
*Assistant Examiner* — Shizhi Qian
(74) *Attorney, Agent, or Firm* — Mattingly & Malur, PC

(57) ABSTRACT

A gas sensor includes: a laminate including at least one layer made of a solid electrolyte; a measured gas flow path formed in the laminate; and a pump electrode exposed in the measured gas flow path. In a part of a rear end side region, the pump electrode is sandwiched between a first layer and a second layer or is covered with a covering layer formed on the inner surface of the measured gas flow path. The area of a portion exposed in the measured gas flow path, of the pump electrode is 4 $mm^2$ or more. The area of a portion exposed in the measured gas flow path, of the front end side region is larger than the area of a portion exposed in the measured gas flow path, of the rear end side region.

9 Claims, 11 Drawing Sheets

(56) References Cited

U.S. PATENT DOCUMENTS

| | | | |
|---|---|---|---|
| 2015/0219591 A1* | 8/2015 | Shimizu | G01N 27/409 |
| | | | 204/426 |
| 2015/0253281 A1 | 9/2015 | Saito et al. | |
| 2018/0284056 A1 | 10/2018 | Watanabe | |
| 2019/0145925 A1 | 5/2019 | Fujii et al. | |
| 2019/0285575 A1* | 9/2019 | Watanabe | G01N 27/307 |

FOREIGN PATENT DOCUMENTS

| | | | |
|---|---|---|---|
| JP | 2010048647 A * | 3/2010 |
| JP | 5204638 B2 | 6/2013 |
| JP | 2018-169328 A | 11/2018 |
| JP | 2019-158866 A | 9/2019 |
| JP | 6697232 B2 | 5/2020 |
| WO | 2018/230703 A1 | 12/2018 |

\* cited by examiner

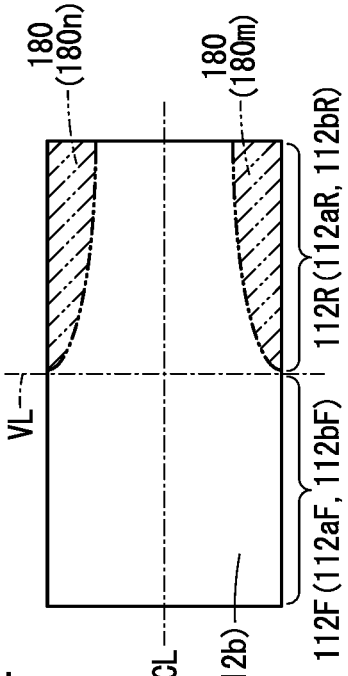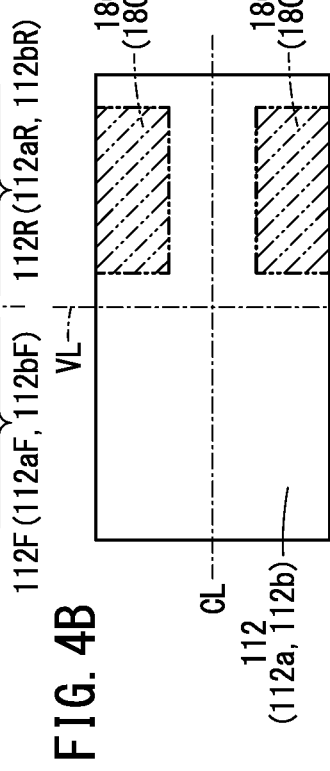

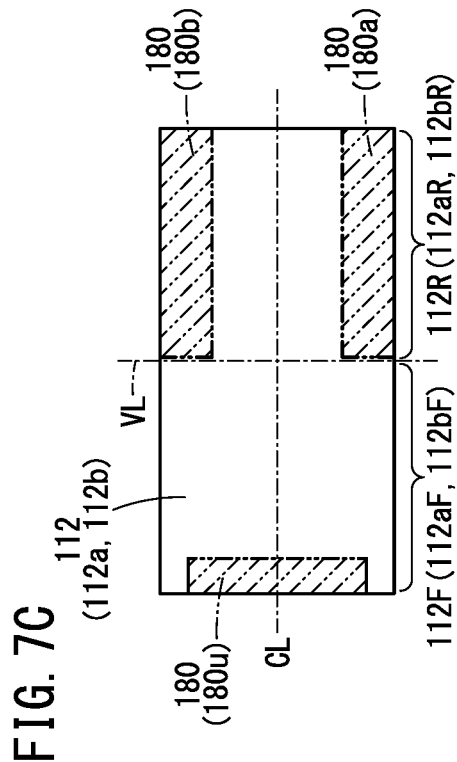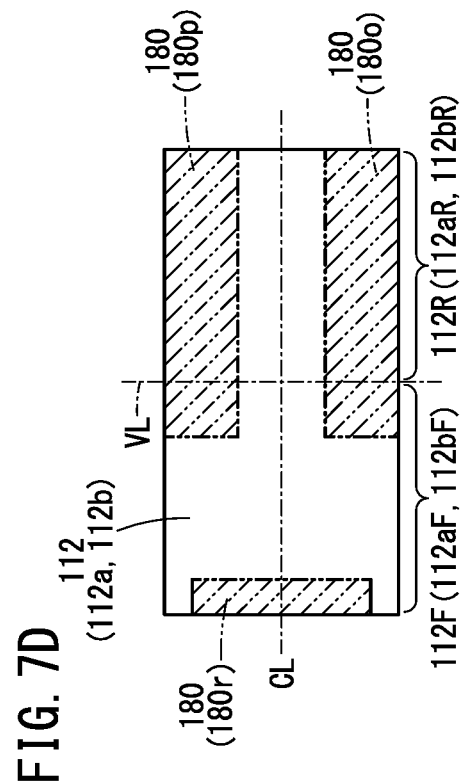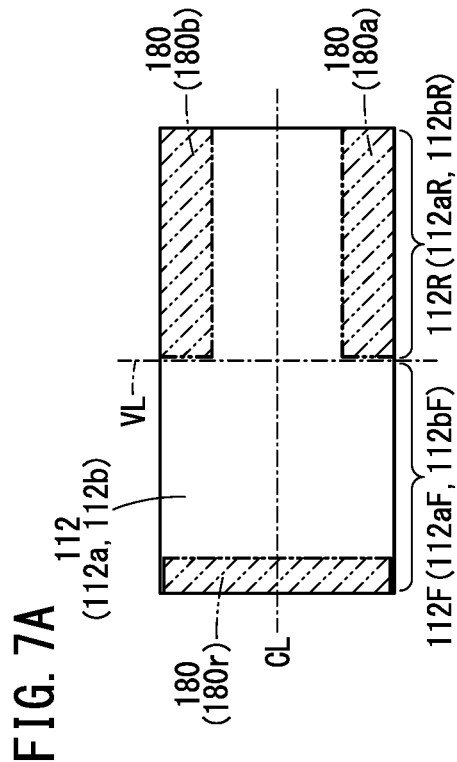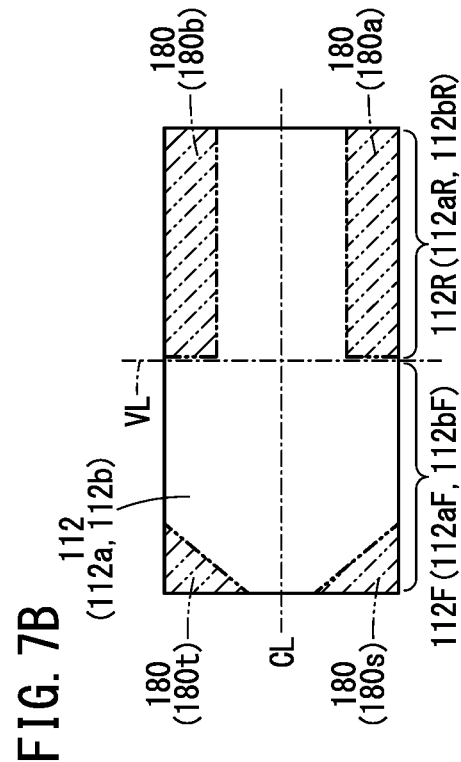

FIG. 9

| | TOTAL AREA OF PUMP ELECTRODE (mm²) | AREA OF SANDWICHED PORTION (mm²) | EFFECTIVE AREA OF PUMP ELECTRODE (mm²) | EFFECTIVE AREA OF FRONT END SIDE REGION (mm²) | EFFECTIVE AREA OF REAR END SIDE REGION (mm²) | LAYOUT OF SANDWICHED PORTION | RATIO OF AREA OF SANDWICHED PORTION TO TOTAL AREA OF PUMP ELECTRODE (%) |
|---|---|---|---|---|---|---|---|
| EXAMPLE 1 | 7.1 | 0.4 | 6.7 | 3.55 | 3.15 | Type A | 6 |
| EXAMPLE 2 | 7.4 | 2.2 | 5.2 | 3.70 | 1.50 | Type A | 30 |
| EXAMPLE 3 | 7.4 | 0.7 | 6.7 | 3.60 | 3.10 | Type B | 9 |
| EXAMPLE 4 | 7.3 | 3.2 | 4.1 | 2.45 | 1.65 | Type B | 44 |
| EXAMPLE 5 | 7.5 | 1.2 | 6.3 | 3.35 | 2.95 | Type B | 16 |
| EXAMPLE 6 | 7.5 | 3.4 | 4.1 | 2.55 | 1.55 | Type B | 45 |
| EXAMPLE 7 | 9.0 | 1.4 | 7.6 | 4.10 | 3.50 | Type B | 16 |
| EXAMPLE 8 | 9.9 | 1.4 | 8.5 | 4.45 | 4.05 | Type B | 14 |
| EXAMPLE 9 | 10.6 | 1.5 | 9.1 | 4.70 | 4.40 | Type B | 14 |
| EXAMPLE 10 | 12.3 | 1.8 | 10.5 | 5.75 | 4.75 | Type B | 15 |
| EXAMPLE 11 | 15.0 | 4.0 | 11.0 | 6.50 | 4.50 | Type B | 27 |
| EXAMPLE 12 | 15.0 | 7.4 | 7.6 | 5.00 | 2.60 | Type B | 49 |
| EXAMPLE 13 | 9.9 | 2.0 | 7.9 | 4.25 | 3.65 | Type B | 20 |
| EXAMPLE 14 | 9.5 | 2.3 | 7.2 | 3.69 | 3.50 | Type C | 24 |
| EXAMPLE 15 | 9.8 | 2.4 | 7.4 | 3.80 | 3.60 | Type C | 24 |
| EXAMPLE 16 | 9.9 | 2.9 | 7.0 | 3.95 | 3.05 | Type C | 29 |
| COMPARATIVE EXAMPLE 1 | 7.5 | 0.0 | 7.5 | 3.75 | 3.75 | NO SANDWICHED PORTION | 0 |
| COMPARATIVE EXAMPLE 2 | 9.9 | 0.0 | 9.9 | 4.95 | 4.95 | NO SANDWICHED PORTION | 0 |
| COMPARATIVE EXAMPLE 3 | 12.3 | 0.0 | 12.3 | 6.15 | 6.15 | NO SANDWICHED PORTION | 0 |
| COMPARATIVE EXAMPLE 4 | 9.8 | 6.5 | 3.3 | 1.65 | 1.65 | ENTIRE PERIPHERAL EDGE PORTION | 66 |
| COMPARATIVE EXAMPLE 5 | 9.8 | 6.5 | 3.3 | 1.60 | 1.70 | ENTIRE PERIPHERAL EDGE PORTION | 66 |

FIG. 10

| | PEELING TEST | PUMP PERFORMANCE TEST | RATIO Q (%) |
|---|---|---|---|
| EXAMPLE 1 | B | A | 53.0 |
| EXAMPLE 2 | A | B | 71.2 |
| EXAMPLE 3 | B | A | 53.7 |
| EXAMPLE 4 | A | B | 59.8 |
| EXAMPLE 5 | A | A | 53.2 |
| EXAMPLE 6 | A | B | 62.2 |
| EXAMPLE 7 | A | A | 53.9 |
| EXAMPLE 8 | A | A | 52.4 |
| EXAMPLE 9 | A | A | 51.6 |
| EXAMPLE 10 | A | A | 54.8 |
| EXAMPLE 11 | A | A | 59.1 |
| EXAMPLE 12 | A | A | 65.8 |
| EXAMPLE 13 | A | A | 53.8 |
| EXAMPLE 14 | A | A | 51.3 |
| EXAMPLE 15 | A | A | 51.4 |
| EXAMPLE 16 | A | A | 56.4 |
| COMPARATIVE EXAMPLE 1 | C | A | 50.0 |
| COMPARATIVE EXAMPLE 2 | C | A | 50.0 |
| COMPARATIVE EXAMPLE 3 | C | A | 50.0 |
| COMPARATIVE EXAMPLE 4 | B | C | 50.0 |
| COMPARATIVE EXAMPLE 5 | B | C | 48.5 |

GAS SENSOR

CROSS-REFERENCE TO RELATED APPLICATION

This application is based upon and claims the benefit of priority from Japanese Patent Application No. 2020-171670 filed on Oct. 12, 2020, the contents of which are incorporated herein by reference.

BACKGROUND OF THE INVENTION

Field of the Invention

The present invention relates to a gas sensor.

Description of the Related Art

JP 2004-151018 A discloses a laminated gas sensor element capable of measuring the concentration of nitrogen oxide ($NO_x$) or the like in a gas to be measured. The laminated gas sensor element disclosed in JP 2004-151018 A includes a measured gas chamber, an oxygen pump cell, and a sensor cell. The measured gas is introduced into the measured gas chamber. The oxygen pump cell has a pump electrode provided so as to face the measured gas chamber. The sensor cell detects the concentration of a specific gas in the measured gas chamber.

SUMMARY OF THE INVENTION

However, in the conventional gas sensor, the pump electrode may be peeled off. If the pump electrode is peeled off, detection accuracy is lowered, and further, detection may become impossible. In order to prevent peeling of the pump electrode, the peripheral edge of the pump electrode may be embedded. However, when the peripheral edge of the pump electrode is simply embedded, good performance is not necessarily obtained.

An object of the present invention is to provide a gas sensor capable of suppressing peeling of a pump electrode while securing good performance.

According to an aspect of the present invention, provided is a gas sensor comprising a laminate comprising a plurality of layers including at least one layer made of a solid electrolyte; a measured gas flow path which is formed in the laminate and through which a measured gas introduced through a gas inlet flows, the gas inlet being located on a front end side that is one side in a longitudinal direction of the laminate; and a pump electrode formed along a longitudinal direction of the measured gas flow path and exposed in the measured gas flow path, wherein the pump electrode includes a front end side region located closer to the front end side than a center of the pump electrode is, and a rear end side region located on a rear end side that is an opposite side of the center of the pump electrode from the front end side, in a part of the rear end side region, the pump electrode is sandwiched between, among the plurality of layers, a first layer and a second layer adjacent to the first layer, or is covered with a covering layer formed on an inner surface of the measured gas flow path, an area of a portion which is exposed in the measured gas flow path, of the pump electrode is 4 $mm^2$ or more, and an area of a portion which is exposed in the measured gas flow path, of the front end side region is larger than an area of a portion which is exposed in the measured gas flow path, of the rear end side region.

According to the present invention, it is possible to provide a gas sensor capable of suppressing peeling of a pump electrode while securing good performance.

The above and other objects, features, and advantages of the present invention will become more apparent from the following description when taken in conjunction with the accompanying drawings, in which a preferred embodiment of the present invention is shown by way of illustrative example.

BRIEF DESCRIPTION OF THE DRAWINGS

FIGS. 4A, 4B, 4C, 4D, 4E, and 4F are plan views each showing an example of the layout of a sandwiched portion;

FIGS. 7A, 7B, 7C, and 7D are plan views each showing an example of the layout of the sandwiched portion;

FIG. 9 is a diagram showing a table illustrating test results;

FIG. 10 is a diagram showing a table illustrating test results; and

DESCRIPTION OF THE PREFERRED EMBODIMENTS

In a conventional gas sensor as disclosed in JP 2004-151018 A, when a pump electrode is repeatedly used over a long period of time, platinum (Pt) contained in the pump electrode is oxidized to form platinum oxide. Platinum oxide is more likely to sublime than platinum. Therefore, when platinum oxide is generated in the pump electrode, the platinum oxide sublimes and the pump electrode is peeled off.

In order to prevent peeling of the pump electrode, the peripheral edge of the pump electrode may be embedded. However, if the peripheral edge of the pump electrode is simply embedded, the area of contact between the pump electrode and the measured gas becomes small, and as a result, the pump voltage increases. If the pump voltage increases, nitrogen oxide is decomposed on the upstream side of the measurement electrode, resulting in a decrease in detection accuracy.

As a result of intensive studies, the inventors of the present application have conceived a gas sensor as described below. According to the gas sensor as described below that has been conceived by the inventors of the present application, it is possible to improve the peeling resistance of the pump electrode while suppressing decomposition of nitrogen oxide on the upstream of the measurement electrode.

The gas sensor according to the present invention will be described below in detail in connection with a preferred embodiment while referring to the accompanying drawings.

EMBODIMENT

Figure 1:
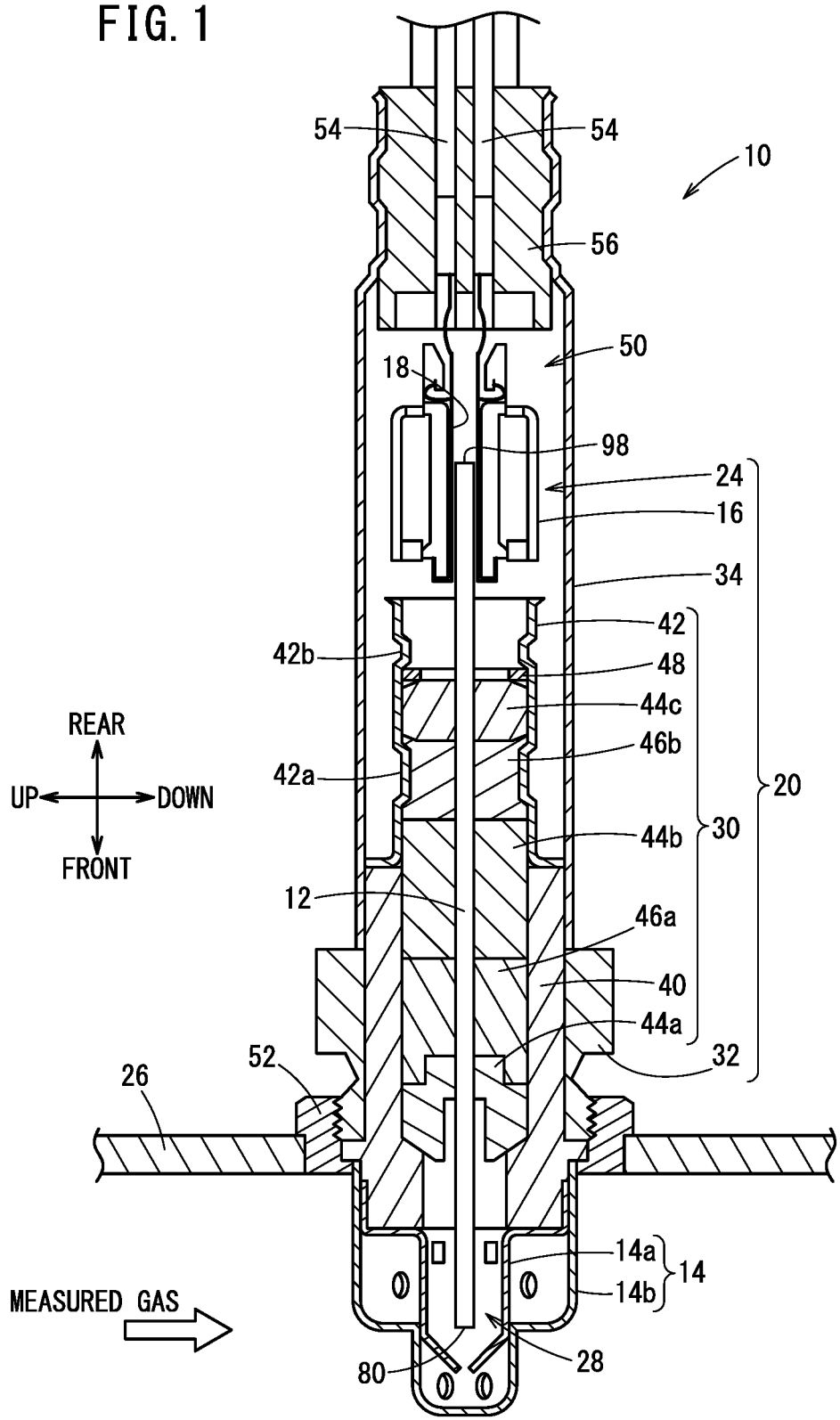
FIG. 1 is a cross-sectional view showing an example of a gas sensor according to an embodiment.
Figure 2:
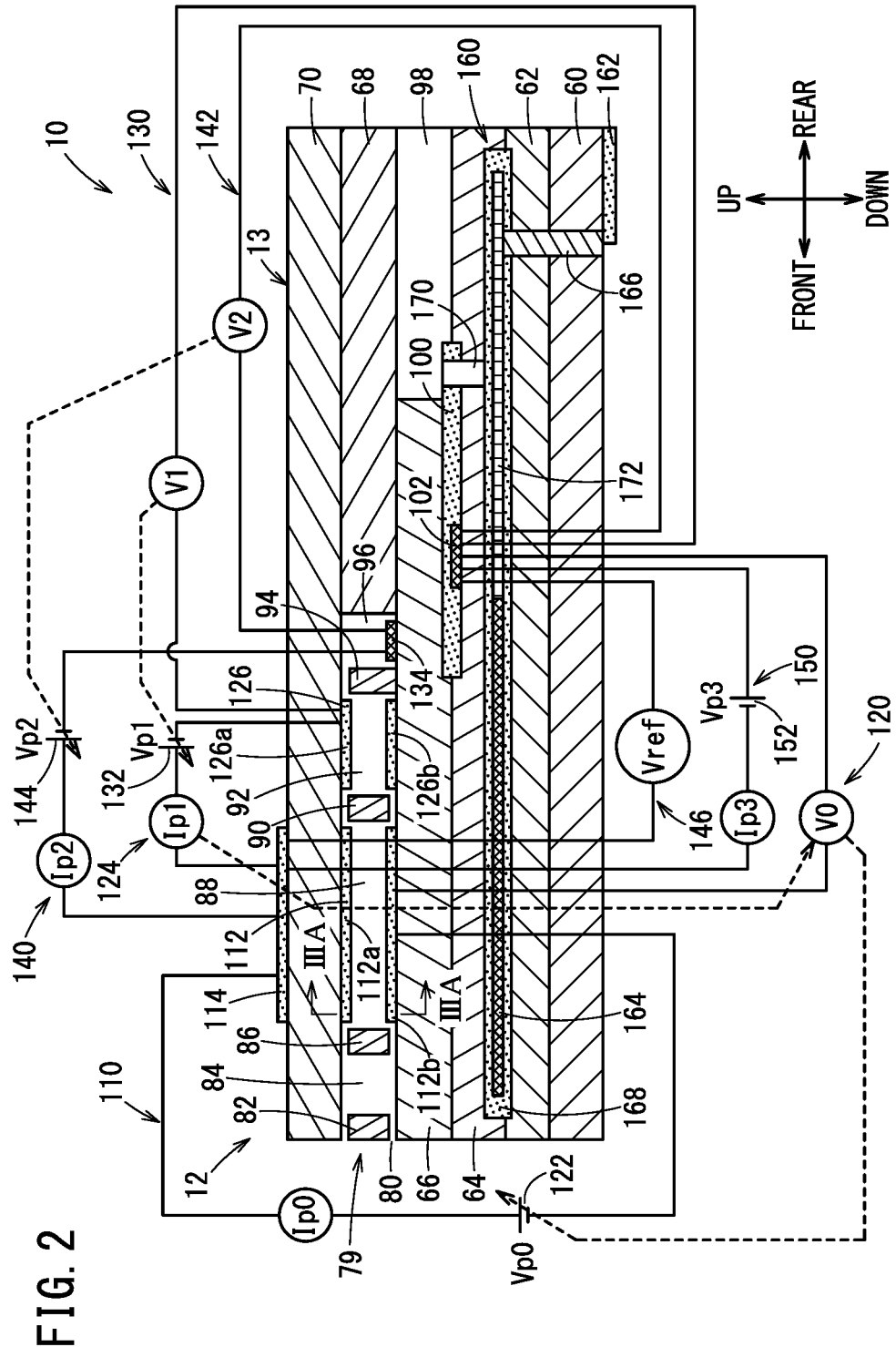
FIG. 2 is a cross-sectional view showing a part of the gas sensor according to the embodiment.

A gas sensor according to an embodiment will be described with reference to FIGS. 1 to 10. FIG. 1 is a cross-sectional view showing an example of a gas sensor according to the present embodiment. FIG. 2 is a cross-sectional view showing a part of the gas sensor according to the present embodiment.

As shown in FIG. 1, a gas sensor 10 includes a sensor element 12. The sensor element 12 has, for example, an elongated rectangular parallelepiped shape. The longitudinal direction of the sensor element 12 is defined as a front-rear direction. That is, the left-right direction in FIG. 2 is defined as the front-rear direction. The thickness direction of the sensor element 12 is defined as an up-down direction. That is, the up-down direction in FIG. 2 is defined as the up-down direction. The width direction of the sensor element 12 is defined as the left-right direction. That is, a direction perpendicular to the front-rear direction and the up-down direction is defined as the left-right direction.

The gas sensor 10 further includes a protective cover 14. The protective cover 14 protects the front end side which is one side in the longitudinal direction of the sensor element 12. The gas sensor 10 further includes a sensor assembly 20 including a ceramic housing 16. Metal terminals 18 are attached to the ceramic housing 16. The metal terminals 18 hold the rear end portion of the sensor element 12 and are electrically connected to the sensor element 12. The metal terminals 18 are attached to the ceramic housing 16 to form a connector 24.

The gas sensor 10 may be attached to a pipe 26, for example. Examples of the pipe 26 include an exhaust gas pipe of a vehicle. The gas sensor 10 can be used to measure the concentration of a specific gas contained in an exhaust gas or the like, which is a measured gas. Examples of the specific gas include, but are not limited to, nitrogen oxides, oxygen ($O_2$), and the like.

The protective cover 14 includes an inner protective cover 14a and an outer protective cover 14b. The inner protective cover 14a is a bottomed tubular protective cover that covers the front end of the sensor element 12. The outer protective cover 14b is a bottomed tubular protective cover that covers the inner protective cover 14a. The inner protective cover 14a and the outer protective cover 14b have formed therein a plurality of holes that allow the measured gas to flow in the interior of the protective cover 14. The front end of the sensor element 12 is located in a space surrounded by the inner protective cover 14a. That is, the front end of the sensor element 12 is located in a sensor element chamber 28.

The sensor assembly 20 includes an element sealing body 30 for sealing and fixing the sensor element 12. The sensor assembly 20 further includes a nut 32 attached to the element sealing body 30. The sensor assembly 20 further includes an outer tube 34 and the connector 24. The metal terminals 18 provided in the connector 24 are connected to electrodes (not shown) formed on the surfaces of the rear end of the sensor element 12. That is, the metal terminals 18 provided in the connector 24 are connected to the electrodes (not shown) formed on the upper surface and the lower surface of the rear end of the sensor element 12.

The element sealing body 30 includes a tubular main fitting 40 and a tubular inner tube 42. The central axis of the main fitting 40 and the central axis of the inner tube 42 coincide with each other. The main fitting 40 and the inner tube 42 are fixed by welding. Ceramic supporters 44a to 44c, green compacts 46a and 46b, and a metal ring 48 are sealed in a through hole inside the main fitting 40 and the inner tube 42. The sensor element 12 is located on the central axis of the element sealing body 30. The sensor element 12 penetrates the element sealing body 30 in the front-rear direction. The inner tube 42 has reduced-diameter portions 42a and 42b. The reduced-diameter portion 42a presses the green compact 46b in a direction toward the central axial of the inner tube 42. The reduced-diameter portion 42b presses forward the ceramic supporters 44a to 44c and the green compacts 46a and 46b via the metal ring 48. The green compacts 46a and 46b are compressed between the main fitting 40 and the sensor element 12 and between the inner tube 42 and the sensor element 12 by the pressing forces from the reduced-diameter portions 42a and 42b. Thus, the green compacts 46a and 46b provide a seal between the sensor element chamber 28 in the protective cover 14 and a space 50 in the outer tube 34, and fix the sensor element 12.

The nut 32 is fixed to the main fitting 40. The central axis of the nut 32 and the central axis of the main fitting 40 coincide with each other. A male screw portion is formed on an outer peripheral surface of the nut 32. A female screw portion is formed on an inner peripheral surface of a fixing member 52 welded to the pipe 26. The male screw portion formed on the outer peripheral surface of the nut 32 is inserted into the fixing member 52 having the female screw portion formed on the inner peripheral surface thereof. Thus, the gas sensor 10 is fixed to the pipe 26 in a state where the front end of the sensor element 12 protected by the protective cover 14 protrudes into the pipe 26.

The outer tube 34 encloses the inner tube 42, the sensor element 12, and the connector 24. A plurality of lead wires 54 connected to the connector 24 are drawn out from the rear end of the outer tube 34 to the outside. The lead wires 54 electrically conduct to electrodes of the sensor element 12 via the connector 24. The gap between the outer tube 34 and the lead wires 54 is sealed by an elastic insulating member 56 formed of a grommet or the like. The space 50 in the outer tube 34 is filled with a reference gas (atmosphere). The rear end of the sensor element 12 is located in the space 50.

As shown in FIG. 2, the sensor element 12 includes a laminate 13 formed of a first substrate layer 60, a second substrate layer 62, a third substrate layer 64, a solid electrolyte layer 66, a spacer layer 68, and a solid electrolyte layer 70. The second substrate layer 62 is laminated on the first substrate layer 60. The third substrate layer 64 is laminated on the second substrate layer 62. The solid electrolyte layer 66 is laminated on the third substrate layer 64. The spacer layer 68 is laminated on the solid electrolyte layer 66. The solid electrolyte layer 70 is laminated on the spacer layer 68. For example, a solid electrolyte is used as the material of these layers 60, 62, 64, 66, 68, and 70. More specifically, an oxygen ion conductive solid electrolyte is used as the material of these layers 60, 62, 64, 66, 68, and 70. Examples of the oxygen ion conductive solid electrolyte include zirconia ($ZrO_2$). These layers 60, 62, 64, 66, 68, 70 are highly airtight. The sensor element 12 can be manufactured as follows. Specifically, predetermined processing, printing of predetermined patterns, and the like are performed on ceramic green sheets corresponding to the respective layers. Thereafter, these ceramic green sheets are laminated. Then, these ceramic green sheets are integrated by firing. In this way, the sensor element 12 can be manufactured. The material of these layers 60, 62, 64, 66, 68, and 70 is not limited to the solid electrolyte. For example, the spacer layer 68 may be an insulator layer or the like. Examples of the insulator layer include alumina and the like.

A measured gas flow path (measured gas flow portion) 79 through which the measured gas flows is formed inside the sensor element 12. The flow direction of the measured gas in the measured gas flow path 79 is the longitudinal direction of the measured gas flow path 79. The measured gas flow path 79 is formed in the spacer layer 68. That is, the measured gas flow path 79 is formed by hollowing out a part of the spacer layer 68. The side surface of the measured gas flow path 79 is defined by the spacer layer 68. The bottom surface (lower surface) of the measured gas flow path 79 is defined by the upper surface of the solid electrolyte layer 66. The top surface (upper surface) of the measured gas flow path 79 is defined by the lower surface of the solid electrolyte layer 70. One end of the measured gas flow path 79 is a gas inlet 80 through which the measured gas is introduced. That is, the gas inlet 80 is on the left side of FIG. 2. The gas inlet 80 is located on the front end side which is one side in the longitudinal direction of the sensor element 12. That is, the gas inlet 80 is located on the front end side which is one side in the longitudinal direction of the laminate 13.

In the measured gas flow path 79, a first diffusion control portion 82 is provided at the rear stage of the gas inlet 80. The first diffusion control portion 82 includes, for example, two slits. The longitudinal direction of the slits is, for example, a direction perpendicular to the drawing sheet of FIG. 2. A buffer space 84 is provided at the rear stage of the first diffusion control portion 82. A second diffusion control portion 86 is provided at the rear stage of the buffer space 84. The second diffusion control portion 86 includes, for example, two slits. The longitudinal direction of the slits is, for example, a direction perpendicular to the drawing sheet of FIG. 2. A first internal cavity 88 is provided at the rear stage of the second diffusion control portion 86. The first internal cavity 88 communicates with the buffer space 84 via the second diffusion control portion 86. A third diffusion control portion 90 is provided at the rear stage of the first internal cavity 88. The third diffusion control portion 90 includes, for example, two slits. The longitudinal direction of the slits is, for example, a direction perpendicular to the drawing sheet of FIG. 2. A second internal cavity 92 is provided at the rear stage of the third diffusion control portion 90. The second internal cavity 92 communicates with the first internal cavity 88 via the third diffusion control portion 90. A fourth diffusion control portion 94 is provided at the rear stage of the second internal cavity 92. The fourth diffusion control portion 94 includes, for example, one slit. The longitudinal direction of the slit is, for example, a direction perpendicular to the drawing sheet of FIG. 2. A third internal cavity 96 is provided at the rear stage of the fourth diffusion control portion 94. The third internal cavity 96 communicates with the second internal cavity 92 via the fourth diffusion control portion 94. At least one of the first diffusion control portion 82, the second diffusion control portion 86, the third diffusion control portion 90, and the fourth diffusion control portion 94 may be formed of a porous body.

A reference gas introduction space 98 is formed inside the sensor element 12. The measured gas flow path 79 described above is located on one side in the longitudinal direction of the sensor element 12. That is, the measured gas flow path 79 is located on the front end side of the sensor element 12. The reference gas introduction space 98 is located on the other side in the longitudinal direction of the sensor element 12. That is, the reference gas introduction space 98 is located on the rear end side of the sensor element 12. The reference gas introduction space 98 is formed by hollowing out a part of the solid electrolyte layer 66. The side surface of the reference gas introduction space 98 is defined by the solid electrolyte layer 66. The lower surface of the reference gas introduction space 98 is defined by the upper surface of the third substrate layer 64. The upper surface of the reference gas introduction space 98 is defined by the lower surface of the spacer layer 68. A reference gas can be introduced into the reference gas introduction space 98. The atmosphere in the space 50 (see FIG. 1) can be the reference gas. The reference gas for measuring the concentration of nitrogen oxide is, for example, atmospheric air.

An atmosphere introduction layer 100 is provided inside the sensor element 12. The atmosphere introduction layer 100 is provided, for example, between the third substrate layer 64 and the solid electrolyte layer 66. A porous material is used as the material of the atmosphere introduction layer 100. More specifically, for example, porous ceramics such as porous alumina can be used as the material of the atmosphere introduction layer 100. A part of the atmosphere introduction layer 100 is exposed in the reference gas introduction space 98. A reference gas can be introduced into the atmosphere introduction layer 100 through the reference gas introduction space 98. The atmosphere introduction layer 100 is formed so as to cover a reference electrode 102 described later. The atmosphere introduction layer 100 allows the reference gas in the reference gas introduction space 98 to reach the reference electrode 102 while applying a predetermined diffusion resistance to the reference gas. A rear end portion of the atmosphere introduction layer 100 is exposed in the reference gas introduction space 98. A portion which covers the reference electrode 102, of the atmosphere introduction layer 100 is not exposed in the reference gas introduction space 98.

The reference electrode 102 is formed on the upper surface of the third substrate layer 64. The reference electrode 102 is formed directly on the third substrate layer 64. An atmosphere introduction layer 100 leading to the reference gas introduction space 98 is formed around the reference electrode 102. The portion of the reference electrode 102 other than the portion thereof in contact with the third substrate layer 64 is covered by the atmosphere introduction layer 100. As will be described later, the oxygen concentration (oxygen partial pressure) in the first internal cavity 88, the oxygen concentration in the second internal cavity 92, and the oxygen concentration in the third internal cavity 96 can be measured using the reference electrode 102. For example, a porous cermet can be used as the material of the reference electrode 102. The cermet is a composite material of ceramic and metal. For example, a cermet of platinum and zirconia can be used as the material of the reference electrode 102.

The gas inlet 80 is open to the external space. The measured gas can be taken into the sensor element 12 from the external space through the gas inlet 80. The first diffusion control portion 82 applies a predetermined diffusion resistance to the measured gas taken in from the gas inlet 80. The buffer space 84 guides the measured gas introduced by the first diffusion control portion 82, to the second diffusion control portion 86. The second diffusion control portion 86 applies a predetermined diffusion resistance to the measured gas introduced from the buffer space 84 into the first internal cavity 88. The measured gas taken into the sensor element 12 through the gas inlet 80 is introduced into the first internal cavity 88 through the first diffusion control portion 82, the buffer space 84, and the second diffusion control portion 86. There is a case where the measured gas is rapidly taken into the sensor element 12 due to pressure fluctuation in the external space. In the case where the measured gas is an automobile exhaust gas, the pressure fluctuation corresponds to the exhaust pressure pulsation. Even when the measured gas is rapidly taken into the sensor element 12 due to the pressure fluctuation in the external space, the concentration fluctuation of the measured gas is canceled while the measured gas passes through the first diffusion control portion 82, the buffer space 84, and the second diffusion control portion 86. Since the measured gas in which the concentration fluctuation is canceled is introduced into the first internal cavity 88, the concentration fluctuation of the measured gas introduced into the first internal cavity 88 is almost negligible. The first internal cavity 88 is a space for adjusting the oxygen partial pressure in the measured gas introduced thereto via the second diffusion control portion 86. The oxygen partial pressure can be adjusted by operation of a main pump cell 110 described later.

The sensor element 12 further includes the main pump cell 110. The main pump cell 110 is an electrochemical pump cell formed of a pump electrode 112, an outer pump electrode 114, and the solid electrolyte layer 70 sandwiched between the pump electrode 112 and the outer pump electrode 114. The pump electrode 112 is disposed in the measured gas flow path 79 so as to extend along the flow direction of the measured gas in the measured gas flow path 79. The outer pump electrode 114 is disposed outside the laminate 13. The pump electrode 112 is formed on the inner surface of the first internal cavity 88. The outer pump electrode 114 is formed on the upper surface of the solid electrolyte layer 70. The outer pump electrode 114 is formed in a region corresponding to a region where the pump electrode 112 is formed. The outer pump electrode 114 is exposed to the external space. That is, the outer pump electrode 114 is exposed in the sensor element chamber 28 in FIG. 1.

The planar shape of the pump electrode 112 is, for example, rectangular. The pump electrode 112 can be formed of a plurality of electrodes respectively formed on the bottom surface of the first internal cavity 88 and the top surface of the first internal cavity 88. That is, the pump electrode 112 can be constituted by a top pump electrode 112a and a bottom pump electrode 112b. The top pump electrode 112a and the bottom pump electrode 112b are electrically connected by patterns or the like (not shown). A center line CL (see FIG. 4A) of the pump electrode 112 in the longitudinal direction coincides with the central axis of the first internal cavity 88 in the longitudinal direction in plan view. The top pump electrode 112a is formed on the top surface of the first internal cavity 88. That is, the top pump electrode 112a is formed on the lower surface of the solid electrolyte layer 70. The bottom pump electrode 112b is formed on the bottom surface of the first internal cavity 88. That is, the bottom pump electrode 112b is formed on the upper surface of the solid electrolyte layer 66.

As the material of the pump electrode 112 and the outer pump electrode 114, for example, a porous cermet can be used. For example, a cermet of platinum and zirconia containing 1% of gold (Au) can be used as the material of the pump electrode 112 and the outer pump electrode 114. As the material of the pump electrode 112 in contact with the measured gas, it is preferable to use a material whose reducing power for nitrogen oxide in the measured gas is weakened. The cermet of platinum and zirconia containing 1% of gold is a material whose reducing power for nitrogen oxide in the measured gas is weakened.

In the main pump cell 110, when a desired pump voltage Vp0 is applied across the pump electrode 112 and the outer pump electrode 114, a pump current Ip0 flows between the pump electrode 112 and the outer pump electrode 114 in the positive direction or negative direction. Accordingly, oxygen in the first internal cavity 88 can be pumped out to the external space, or oxygen in the external space can be pumped into the first internal cavity 88.

The sensor element 12 further includes an oxygen-partial-pressure detection sensor cell (main-pump-controlling oxygen-partial-pressure detection sensor cell) 120. The oxygen-partial-pressure detection sensor cell 120 is an electrochemical sensor cell for detecting the oxygen concentration (oxygen partial pressure) in the atmosphere in the first internal cavity 88. The oxygen-partial-pressure detection sensor cell 120 is formed of the pump electrode 112, the solid electrolyte layers 66 and 70, the spacer layer 68, and the reference electrode 102.

By detecting an electromotive force V0 in the oxygen-partial-pressure detection sensor cell 120, the oxygen concentration in the atmosphere in the first internal cavity 88 can be ascertained. Further, the pump current Ip0 can be controlled by feedback controlling the pump voltage Vp0 of a variable power supply 122 so that the electromotive force V0 is kept constant. Thus, the oxygen concentration in the first internal cavity 88 can be maintained at a predetermined constant value.

The third diffusion control portion 90 applies a predetermined diffusion resistance to the measured gas introduced from the first internal cavity 88 to the second internal cavity 92, and guides the measured gas to the second internal cavity 92. As described above, the oxygen concentration in the atmosphere in the first internal cavity 88 can be controlled by the main pump cell 110. The third diffusion control portion 90 applies a predetermined diffusion resistance to the measured gas whose oxygen concentration has been controlled by the main pump cell 110.

The second internal cavity 92 is a space for further adjusting the oxygen concentration of the measured gas whose oxygen concentration has been adjusted in advance in the first internal cavity 88. That is, the oxygen concentration of the measured gas introduced into the second internal cavity 92 via the third diffusion control portion 90 is further adjusted. Further adjustment of the oxygen concentration can be performed in the second internal cavity 92 by an auxiliary pump cell 124 described later. Since the oxygen concentration in the second internal cavity 92 can be kept constant with high accuracy, the gas sensor 10 can measure the concentration of nitrogen oxide with high accuracy.

The sensor element 12 further includes the auxiliary pump cell 124. The auxiliary pump cell 124 is an auxiliary electrochemical pump cell. The auxiliary pump cell 124 is formed of an auxiliary pump electrode 126, the outer pump electrode 114, and the solid electrolyte layer 70. The auxiliary pump electrode 126 is formed on the inner surface of the second internal cavity 92. Note that an outer electrode provided separately from the outer pump electrode 114 may be used for the auxiliary pump cell 124.

The auxiliary pump electrode 126 is formed in a tubular shape. The center line of the auxiliary pump electrode 126 in the longitudinal direction coincides with the central axis of the second internal cavity 92 in the longitudinal direction in plan view. The auxiliary pump electrode 126 is configured by integrally forming a top electrode portion 126a, a bottom electrode portion 126b, and side electrode portions (not shown). The top electrode portion 126a is formed on the top surface of the second internal cavity 92. That is, the top electrode portion 126a is formed on the lower surface of the solid electrolyte layer 70. The bottom electrode portion 126b is formed on the bottom surface of the second internal cavity 92. That is, the bottom electrode portion 126b is formed on the upper surface of the solid electrolyte layer 66. The side electrode portions are formed on side wall portions on both sides of the second internal cavity 92. That is, the side electrode portions are formed on the side wall surfaces (inner surfaces) of the spacer layer 68. Like the pump electrode 112, the auxiliary pump electrode 126 is preferably made of a material whose reducing power for nitrogen oxide in the measured gas is weakened.

In the auxiliary pump cell 124, when a voltage Vp1 is applied across the auxiliary pump electrode 126 and the outer pump electrode 114 by a variable power supply 132, a pump current Ip1 flows between the auxiliary pump electrode 126 and the outer pump electrode 114 in the positive direction or negative direction. Accordingly, oxygen in the second internal cavity 92 can be pumped out to the external space, or oxygen in the external space can be pumped into the second internal cavity 92.

The sensor element 12 further includes an oxygen-partial-pressure detection sensor cell (auxiliary-pump-controlling oxygen-partial-pressure detection sensor cell) 130. The oxygen-partial-pressure detection sensor cell 130 is an electrochemical sensor cell for controlling the oxygen concentration in the atmosphere in the second internal cavity 92. The oxygen-partial-pressure detection sensor cell 130 includes the auxiliary pump electrode 126, the reference electrode 102, the solid electrolyte layers 66 and 70, and the spacer layer 68.

The voltage Vp1 is controlled based on an electromotive force V1 detected by the oxygen-partial-pressure detection sensor cell 130. As described above, in the auxiliary pump cell 124, the pump current Ip1 flows between the auxiliary pump electrode 126 and the outer pump electrode 114 in accordance with the voltage Vp1 applied across the auxiliary pump electrode 126 and the outer pump electrode 114. Thus, pumping of oxygen can be performed. The oxygen partial pressure in the atmosphere in the second internal cavity 92 can be controlled to such low partial pressure as not to substantially affect the measurement of the concentration of nitrogen oxide.

A signal indicating the pump current Ip1 can be input to the oxygen-partial-pressure detection sensor cell 120. The oxygen-partial-pressure detection sensor cell 120 controls a signal indicating the electromotive force V0 based on the signal indicating the pump current Ip1. In this manner, control is thus provided so that the gradient of the oxygen partial pressure in the measured gas introduced into the second internal cavity 92 via the third diffusion control portion 90 is always constant. In the case where the gas sensor 10 is used as a gas sensor that measures the concentration of nitrogen oxide, the oxygen concentration in the atmosphere in the second internal cavity 92 can be set to a constant value of, for example, about 0.001 ppm by the operation of the main pump cell 110 and the auxiliary pump cell 124.

The fourth diffusion control portion 94 applies a predetermined diffusion resistance to the measured gas introduced from the second internal cavity 92 to the third internal cavity 96, and guides the measured gas to the third internal cavity 96. As described above, the oxygen concentration in the atmosphere in the second internal cavity 92 can be controlled by the auxiliary pump cell 124. The fourth diffusion control portion 94 applies a predetermined diffusion resistance to the measured gas whose oxygen concentration has been controlled by the auxiliary pump cell 124. The fourth diffusion control portion 94 also serves to limit the amount of nitrogen oxide flowing into the third internal cavity 96.

The measured gas whose oxygen concentration has been adjusted in advance in the second internal cavity 92 is introduced into the third internal cavity 96 via the fourth diffusion control portion 94. The third internal cavity 96 is a space for detecting the concentration of nitrogen oxide in the measured gas. That is, the third internal cavity 96 is a space for detecting the concentration of nitrogen oxide. The concentration of nitrogen oxide can be measured by operating a measurement pump cell 140 described later.

The sensor element 12 further includes the measurement pump cell 140. The measurement pump cell 140 is an electrochemical pump cell for measuring the concentration of nitrogen oxide in the measured gas introduced into the third internal cavity 96. The measurement pump cell 140 is formed of a measurement electrode 134, the outer pump electrode 114, the solid electrolyte layers 66 and 70, and the spacer layer 68. The measurement electrode 134 is formed on the upper surface of the solid electrolyte layer 66. As the material of the measurement electrode 134, for example, a porous cermet can be used. The measurement electrode 134 functions as a catalyst for reducing nitrogen oxide present in the atmosphere in the third internal cavity 96.

The measurement pump cell 140 pumps out oxygen generated by decomposition of nitrogen oxide in the atmosphere around the measurement electrode 134. A pump current Ip2 corresponding to the amount of oxygen pumped out by the measurement pump cell 140 can be detected.

The sensor element 12 further includes an oxygen-partial-pressure detection sensor cell (measurement-pump-controlling oxygen-partial-pressure detection sensor cell) 142. The oxygen-partial-pressure detection sensor cell 142 is an electrochemical sensor cell for detecting the oxygen partial pressure around the measurement electrode 134. The oxygen-partial-pressure detection sensor cell 142 is formed of the solid electrolyte layer 66, the measurement electrode 134, and the reference electrode 102. A variable power supply 144 can be controlled based on an electromotive force V2 detected by the oxygen-partial-pressure detection sensor cell 142.

The measured gas guided into the second internal cavity 92 reaches the measurement electrode 134 in the third internal cavity 96 via the fourth diffusion control portion 94 under the condition that the oxygen partial pressure is controlled. The nitrogen oxide in the measured gas around the measurement electrode 134 is reduced by the measurement electrode 134 ($2NO \rightarrow N_2 + O_2$), and oxygen is generated around the measurement electrode 134. The generated oxygen is pumped by the measurement pump cell 140. At this time, the voltage Vp2 of the variable power supply 144 is controlled so that the electromotive force V2 detected by the oxygen-partial-pressure detection sensor cell 142 is kept constant. The amount of oxygen generated around the measurement electrode 134 is proportional to the concentration of nitrogen oxide in the measured gas. Therefore, the concentration of the nitrogen oxide in the measured gas can be calculated based on the pump current Ip2 in the measurement pump cell 140.

The sensor element 12 further includes a sensor cell 146. The sensor cell 146 is an electrochemical sensor cell formed of the third substrate layer 64, the solid electrolyte layers 66 and 70, the spacer layer 68, the outer pump electrode 114, and the reference electrode 102. The oxygen partial pressure in the measured gas outside the sensor element 12 can be detected based on an electromotive force Vref obtained by the sensor cell 146.

The sensor element 12 further includes a reference gas adjustment pump cell 150. The reference gas adjustment pump cell 150 is an electrochemical pump cell formed of the third substrate layer 64, the solid electrolyte layers 66 and 70, the spacer layer 68, the outer pump electrode 114, and the reference electrode 102. The reference gas adjustment pump cell 150 performs pumping as a voltage Vp3 applied by a variable power supply 152 connected between the outer pump electrode 114 and the reference electrode 102 causes a control current Ip3 to flow. The reference gas adjustment pump cell 150 can pump oxygen into the atmosphere introduction layer 100 located around the reference electrode 102, from the sensor element chamber 28 (see FIG. 1) located around the outer pump electrode 114. The voltage Vp3 of the variable power supply 152 is a DC voltage such that the control current Ip3 has a predetermined value, and is determined in advance. That is, the voltage Vp3 of the variable power supply 152 is determined in advance as a DC voltage such that the control current Ip3 becomes a DC current with a constant value.

In this gas sensor 10, the main pump cell 110 and the auxiliary pump cell 124 operate to supply, to the measurement pump cell 140, the measured gas whose oxygen partial pressure is kept at a constant low value. That is, the measured gas whose oxygen partial pressure is kept at a value that does not substantially affect the measurement of the concentration of nitrogen oxide is supplied to the measurement pump cell 140. Then, oxygen in an amount substantially proportional to the concentration of the nitrogen oxide in the measured gas is generated by reduction of the nitrogen oxide. The oxygen thus generated is pumped out by the measurement pump cell 140. Since the pump current Ip2 flows in accordance with the amount of oxygen pumped out by the measurement pump cell 140, the concentration of the nitrogen oxide in the measured gas can be detected based on the pump current Ip2.

The sensor element 12 further includes a heater unit 160 for heating the sensor element 12 and keeping the temperature thereof. The heater unit 160 serves to adjust the temperature of the sensor element 12. By heating the solid electrolyte provided in the sensor element 12, the oxygen ion conductivity of the solid electrolyte can be increased. The heater unit 160 includes a heater connector electrode 162, a heater 164, a through hole 166, a heater insulating layer 168, a pressure release hole 170, and a lead wire 172.

The heater connector electrode 162 is formed, for example, on the lower surface of the first substrate layer 60. By electrically connecting the heater connector electrode 162 to an external power supply, power can be supplied from the external power supply to the heater unit 160.

The heater 164 is sandwiched between the second substrate layer 62 and the third substrate layer 64 from above and below. The heater 164 is formed of, for example, an electric resistor. The heater 164 is connected to the heater connector electrode 162 via the lead wire 172 and the through hole 166. The heater 164 generates heat by being supplied with power from the outside via the heater connector electrode 162. The heater 164 can heat and keep the temperature of the solid electrolyte forming the sensor element 12.

In plan view, the region from the first internal cavity 88 to the third internal cavity 96 overlaps the region in which the heater 164 is formed. Therefore, a portion which needs to be activated, of the solid electrolyte provided in the sensor element 12 can be sufficiently activated by the heater 164.

The heater insulating layer 168 is formed so as to cover the upper surface, the lower surface, and the side surfaces of the heater 164. As the material of the heater insulating layer 168, for example, an insulator can be used. More specifically, for example, porous alumina or the like can be used as the material of the heater insulating layer 168. The heater insulating layer 168 is provided to ensure electrical insulation between the second substrate layer 62 and the heater 164 and electrical insulation between the third substrate layer 64 and the heater 164.

The pressure release hole 170 penetrates through the third substrate layer 64 and the atmosphere introduction layer 100 and communicates with the reference gas introduction space 98. The pressure release hole 170 is formed for the purpose of reducing an increase in internal pressure due to an increase in temperature of the heater insulating layer 168.

The variable power supplies 122, 132, 144, 152 and the like are actually connected to the respective electrodes via lead wires (not shown) formed in the sensor element 12, the connector 24 (see FIG. 1), and the lead wires 54 (see FIG. 1).

Figure 3A:
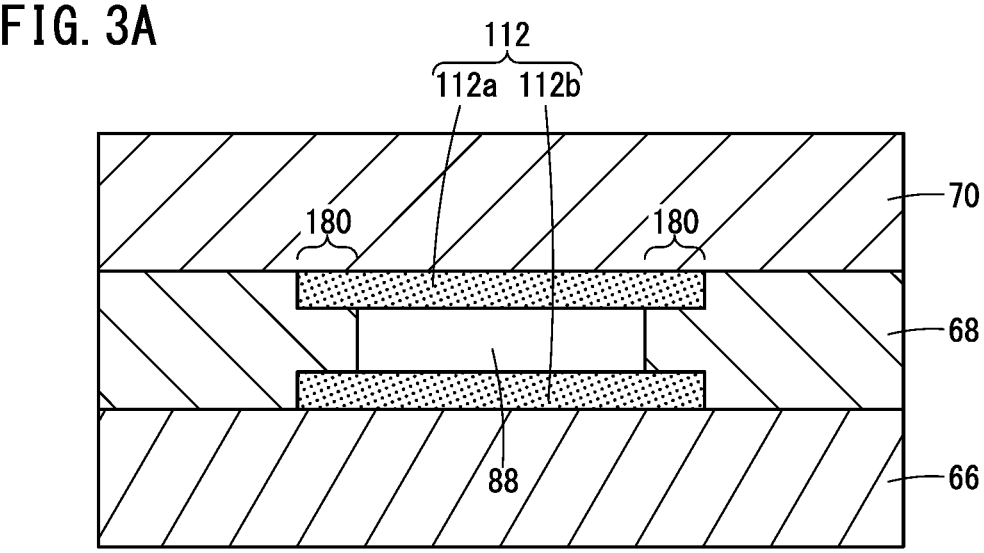
FIGS. 3A and 3B are cross-sectional views each showing an example of a part of a sensor element according to an embodiment.
Figure 3B:
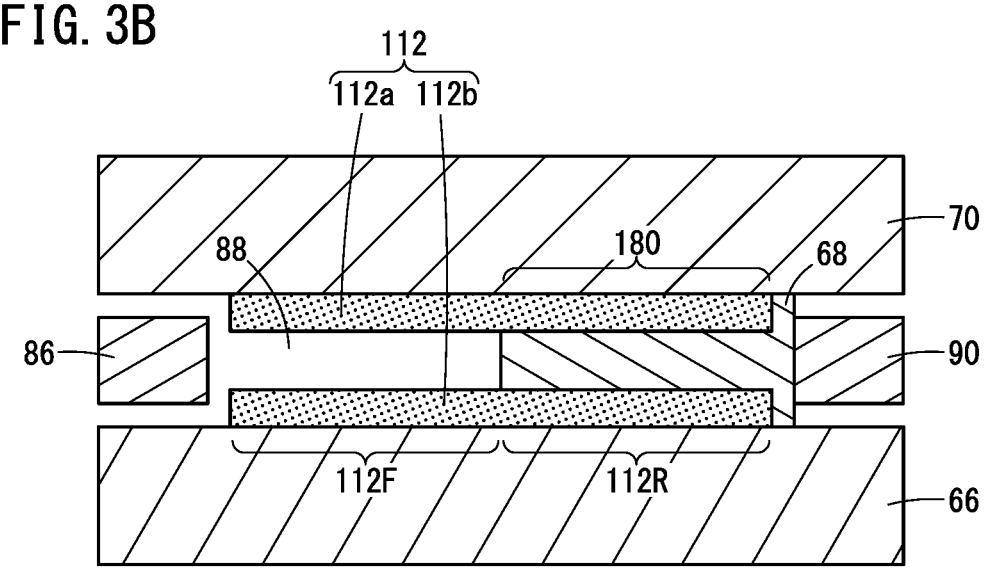

FIGS. 3A and 3B are cross-sectional views each showing an example of a part of the sensor element according to the present embodiment. FIG. 3A corresponds to a cross section taken along line IIIA-IIIA of FIG. 2. FIG. 3B shows a cross section along the longitudinal direction of the sensor element 12. FIG. 4A is a plan view showing an example of the layout of a sandwiched portion described later.

As shown in FIGS. 3A and 3B, the top pump electrode 112a is formed on the top surface of the first internal cavity 88. The bottom pump electrode 112b is formed on the bottom surface of the first internal cavity 88. The top pump electrode 112a and the bottom pump electrode 112b constitute the pump electrode 112. The center lines of the top pump electrode 112a and the bottom pump electrode 112b in the longitudinal direction coincide with the central axis of the first internal cavity 88 in the longitudinal direction in plan view. That is, the center line CL of the pump electrode 112 in the longitudinal direction coincides with the central axis of the first internal cavity 88 in the longitudinal direction in plan view. Note that the central axis of the first internal cavity 88 in the longitudinal direction coincides with the central axis of the measured gas flow path 79 in the longitudinal direction.

When the pump electrode 112 is divided into two equal parts by an imaginary line VL intersecting the longitudinal direction of the measured gas flow path 79, the pump electrode 112 is as follows. More specifically, when the pump electrode 112 is divided into two equal parts by the imaginary line VL orthogonal to the longitudinal direction of the measured gas flow path 79, the pump electrode 112 is as follows. That is, in this case, as shown in FIG. 4A, the pump electrode 112 is divided into a front end side region 112F located on the front end side, and a rear end side region 112R located on the rear end side opposite to the front end side. In other words, the pump electrode 112 includes the front end side region 112F located closer to the front end side than the center of the pump electrode 112 is, and the rear end side region 112R located closer to the rear end side than the center of the pump electrode 112 is. As described above, the pump electrode 112 can be constituted by the top pump electrode 112a and the bottom pump electrode 112b. The top pump electrode 112a includes a front end side region 112aF and a rear end side region 112aR. The bottom pump electrode 112b includes a front end side region 112bF and a rear end side region 112bR.

As shown in FIGS. 3A and 3B, at least a part of the pump electrode 112 is embedded in the laminate 13 (see FIG. 2). That is, as shown in FIGS. 3A and 3B, at least a part of the pump electrode 112 is sandwiched between the spacer layer 68 and the solid electrolyte layers 66 and 70. More specifically, as shown in FIG. 3B, the pump electrode 112 is sandwiched between the spacer layer 68 and the solid electrolyte layers 66 and 70 in a part of the rear end side region 112R. That is, the top pump electrode 112a is sandwiched between the spacer layer 68 and the solid electrolyte layer 70 in a part of the rear end side region 112aR (see FIG. 4A). The bottom pump electrode 112b is sandwiched between the spacer layer 68 and the solid electrolyte layer 66 in a part of the rear end side region 112bR (see FIG. 4A). A portion which is sandwiched by the laminate 13, of the pump electrode 112 is referred to as a sandwiched portion. In the present embodiment, a part of the pump electrode 112 is sandwiched between the spacer layer 68 and the solid electrolyte layers 66 and 70 for the following reason. That is, when the pump electrode 112 is repeatedly used over a long period of time, platinum contained in the pump electrode 112 may be oxidized to form platinum oxide. In a severe use environment such as a high temperature, platinum is more likely to be oxidized, and thus platinum oxide is more likely to be generated. Platinum oxide is more likely to sublime than platinum. Therefore, when platinum oxide is generated in the pump electrode 112, the platinum oxide may sublime and peeling may occur at the interface between the pump electrode 112 and the solid electrolyte layers 66 and 70. Therefore, in this embodiment, in order to prevent the peeling of the pump electrode 112, a part of the pump electrode 112 is sandwiched between the spacer layer 68 and the solid electrolyte layers 66 and 70.

In the example shown in FIG. 4A, a sandwiched portion 180 is located on each of both sides of the center line CL of the pump electrode 112. That is, in the example shown in FIG. 4A, sandwiched portions 180a and 180b are located on both sides of the center line CL of the pump electrode 112. Reference numeral 180 is used to describe the sandwiched portion in general, and reference numerals 180a and 180b are used to describe the individual sandwiched portions. The longitudinal direction of the sandwiched portions 180a and 180b is a direction along the longitudinal direction of the pump electrode 112. In the example shown in FIG. 4A, the front ends of the sandwiched portions 180a and 180b coincide with the imaginary line VL dividing the pump electrode 112 into two equal parts. In the example shown in FIG. 4A, the rear ends of the sandwiched portions 180a and 180b coincide with the rear end of the pump electrode 112. In the example shown in FIG. 4A, the sandwiched portion 180 is disposed only in the rear end side region 112R of the pump electrode 112. Such a layout in which the sandwiched portion 180 is disposed only in the rear end side region 112R of the pump electrode 112 is referred to as the layout of type A.

In order to prevent peeling of the pump electrode 112, it is preferable to secure a certain amount of area of the sandwiched portion 180. Specifically, the ratio of the area of the sandwiched portion 180 to the total area of the pump electrode 112 is preferably 5% or more. Further, the ratio of the area of the sandwiched portion 180 to the total area of the pump electrode 112 is more preferably 10% or more.

If the area of the sandwiched portion 180 is excessively large, cracks occur in the pump electrode 112 due to a difference in thermal expansion coefficient between the pump electrode 112 and the solid electrolyte layers 66 and 70. Therefore, it is preferable that the area of the sandwiched portion 180 is not excessively large. Specifically, the ratio of the area of the sandwiched portion 180 to the total area of the pump electrode 112 is preferably 50% or less.

For this reason, the ratio of the area of the sandwiched portion 180 to the total area of the pump electrode 112 is preferably 5% to 50%, and more preferably 10% to 50%. That is, the ratio of the area of the portion which is not exposed in the measured gas flow path 79, of the pump electrode 112 to the total area of the pump electrode 112 is preferably 5% to 50%, and more preferably 10% to 50%.

Further, in the present embodiment, in order to obtain a sufficient pump performance, the area of the portion which is exposed in the measured gas flow path 79, of the pump electrode 112 is set to be 4 mm$^2$ or more. As described above, the pump electrode 112 is constituted by the top pump electrode 112a and the bottom pump electrode 112b. Therefore, the area of the portion which is exposed in the measured gas flow path 79, of the top pump electrode 112a is set to be 2 mm$^2$ or more, for example, and the area of the portion which is exposed in the measured gas flow path 79, of the bottom pump electrode 112b is set to be 2 mm$^2$ or more, for example.

In the present embodiment, the area of the portion which is exposed in the measured gas flow path 79, of the front end side region 112F is larger than the area of the portion which is exposed in the measured gas flow path 79, of the rear end side region 112R. This is because of the following reasons. Specifically, the oxygen concentration of the measured gas in the front end side region 112F is higher than the oxygen concentration of the measured gas in the rear end side region 112R. Ensuring a large exposed area of the pump electrode 112 in a region having a higher oxygen concentration contributes to ensuring a sufficient pump performance. On the other hand, when the area of the portion which is exposed in the measured gas flow path 79, of the front end side region 112F is significantly smaller than the area of the portion which is exposed in the measured gas flow path 79, of the rear end side region 112R, the following occurs. Specifically, in such a case, it is impossible to obtain an electromotive force V0 that accurately reflects the oxygen concentration in the atmosphere in the first internal cavity 88, resulting in an excessive increase in the pump voltage Vp0. If the pump voltage Vp0 is excessively increased, the oxygen concentration in the atmosphere in the first internal cavity 88 is not appropriately controlled, resulting in decomposition of nitrogen oxide, and thus the concentration of nitrogen oxide cannot be detected accurately. For this reason, in the present embodiment, the area of the portion which is exposed in the measured gas flow path 79, of the front end side region 112F is larger than the area of the portion which is exposed in the measured gas flow path 79, of the rear end side region 112R.

Figure 5A:
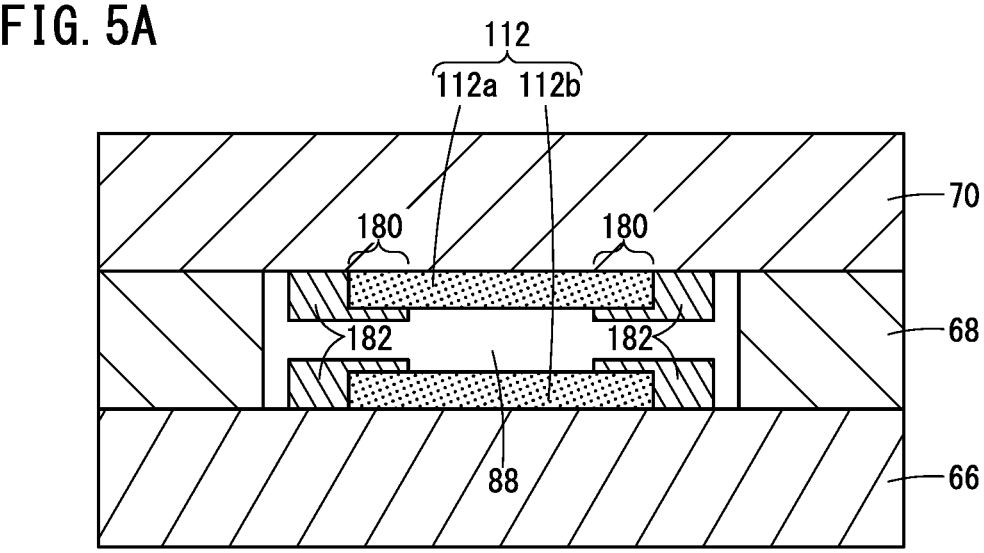
FIGS. 5A and 5B are cross-sectional views each showing an example of a part of the sensor element according to the embodiment.
Figure 5B:
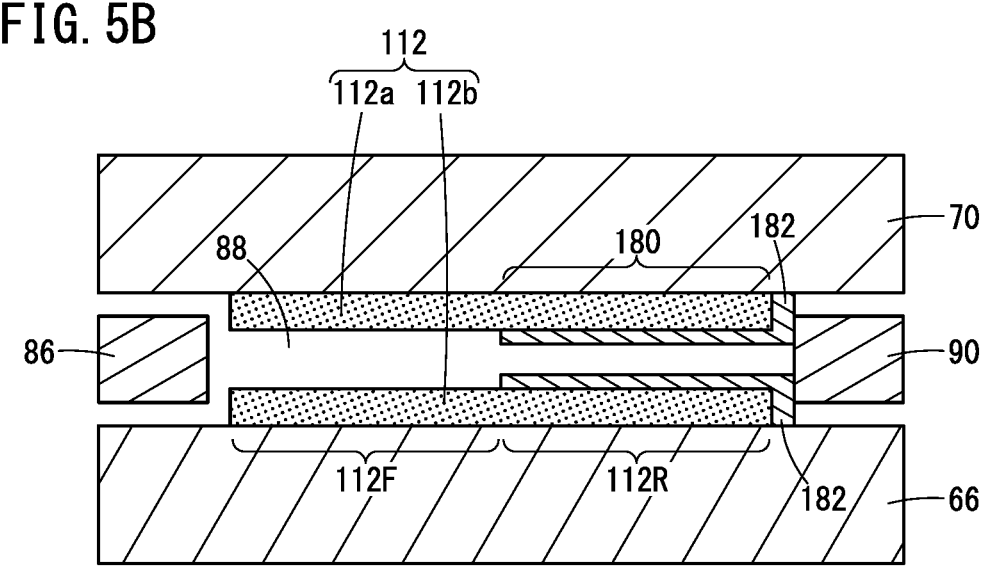

FIGS. 5A and 5B are cross-sectional views each showing an example of a part of the sensor element according to the present embodiment. FIG. 5A corresponds to a cross section taken along line IIIA-IIIA of FIG. 2. FIG. 5B shows a cross section along the longitudinal direction of the sensor element 12.

In the examples shown in FIGS. 5A and 5B, a part of the rear end side region 112R of the pump electrode 112 is covered with a part of a covering layer 182 formed on the inner surface of the measured gas flow path 79 (see FIG. 2). The portion which is covered with the covering layer 182, of the pump electrode 112 is sandwiched between the solid electrolyte layers 66 and 70 and the covering layer 182. That is, in the examples shown in FIGS. 5A and 5B, the portion which is covered with the covering layer 182, of the pump electrode 112 is the sandwiched portion 180 (see FIG. 4A). Also in the examples shown in FIGS. 5A and 5B, similarly to the examples shown in FIGS. 3A and 3B, the sandwiched portion 180 can be disposed in the layout shown in FIG. 4A.

FIG. 4B is a plan view showing an example of the layout of the sandwiched portion.

In the example shown in FIG. 4B, the sandwiched portion 180 is located on each of both sides of the center line CL of the pump electrode 112. That is, in the example shown in FIG. 4B, sandwiched portions 180c and 180d are located on both sides of the center line CL of the pump electrode 112. The longitudinal direction of the sandwiched portions 180c and 180d is a direction along the longitudinal direction of the pump electrode 112. In the example shown in FIG. 4B, the front ends of the sandwiched portions 180c and 180d are located closer to the rear end side than the imaginary line VL is, the imaginary line dividing the pump electrode 112 into two equal parts. In the example shown in FIG. 4B, the rear ends of the sandwiched portions 180c and 180d are located closer to the front end side than the rear end of the pump electrode 112 is. In the example shown in FIG. 4B, the sandwiched portion 180 is disposed only in the rear end side region 112R of the pump electrode 112. Therefore, the layout shown in FIG. 4B belongs to type A.

FIG. 4C is a plan view showing an example of the layout of the sandwiched portion.

In the example shown in FIG. 4C, the sandwiched portion 180 is located on each of both sides of the center line CL of the pump electrode 112. That is, in the example shown in FIG. 4C, sandwiched portions 180e and 180f are located on both sides of the center line CL of the pump electrode 112. The longitudinal direction of the sandwiched portions 180e and 180f is a direction along the longitudinal direction of the pump electrode 112. Further, in the example shown in FIG. 4C, the sandwiched portion 180 is further located at the end portion of the pump electrode 112 on the rear end side. That is, in the example shown in FIG. 4C, a sandwiched portion 180g is further located at the end portion of the pump electrode 112 on the rear end side. The longitudinal direction of the sandwiched portion 180g is orthogonal to the longitudinal direction of the pump electrode 112. The dimension of the sandwiched portion 180g in the direction orthogonal to the longitudinal direction of the pump electrode 112 is equal to the dimension of the pump electrode 112 in the direction orthogonal to the longitudinal direction of the pump electrode 112. In the example shown in FIG. 4C, in plan view, the rear ends of the sandwiched portions 180e and 180f reach a region where the sandwiched portion 180g is disposed. In the example shown in FIG. 4C, the front ends of the sandwiched portions 180e and 180f coincide with the imaginary line VL dividing the pump electrode 112 into two equal parts. In the example shown in FIG. 4C, the sandwiched portion 180 is disposed only in the rear end side region 112R of the pump electrode 112. Therefore, the layout shown in FIG. 4C belongs to type A.

FIG. 4D is a plan view showing the layout of the sandwiched portion.

In the example shown in FIG. 4D, the sandwiched portion 180 is located on each of both sides of the center line CL of the pump electrode 112. That is, in the example shown in FIG. 4D, sandwiched portions 180h and 180i are located on both sides of the center line CL of the pump electrode 112. The longitudinal direction of the sandwiched portions 180h and 180i is a direction along the longitudinal direction of the pump electrode 112. In the example shown in FIG. 4D, the planar shape of the sandwiched portions 180h and 180i is triangular. In the example shown in FIG. 4D, the widths of the sandwiched portions 180h and 180i gradually increase from the front end side toward the rear end side of the sensor element 12. In the example shown in FIG. 4D, the distance between the sandwiched portion 180h and the sandwiched portion 180i decreases from the front end side toward the rear end side of the sensor element 12. In the example shown in FIG. 4D, the sandwiched portion 180 is disposed only in the rear end side region 112R of the pump electrode 112. Therefore, the layout shown in FIG. 4D belongs to type A.

FIG. 4E is a plan view showing an example of the layout of the sandwiched portion.

In the example shown in FIG. 4E, the sandwiched portion 180 is located on each of both sides of the center line CL of the pump electrode 112. That is, in the example shown in FIG. 4E, sandwiched portions 180j and 180k are located on both sides of the center line CL of the pump electrode 112. The longitudinal direction of the sandwiched portions 180j and 180k is a direction along the longitudinal direction of the pump electrode 112. In the example shown in FIG. 4E, the rear ends of the sandwiched portions 180j and 180k are located closer to the front end side than the rear end of the pump electrode 112 is. In the example shown in FIG. 4E, the sandwiched portion 180 is further located at the end portion of the pump electrode 112 on the rear end side. That is, in the example shown in FIG. 4E, a sandwiched portion 180l is further located at the end portion of the pump electrode 112 on the rear end side. The longitudinal direction of the sandwiched portion 180l is orthogonal to the longitudinal direction of the pump electrode 112. The dimension of the sandwiched portion 180l in the direction orthogonal to the longitudinal direction of the pump electrode 112 is smaller than the dimension of the pump electrode 112 in the direction orthogonal to the longitudinal direction of the pump electrode 112. In the example shown in FIG. 4E, the sandwiched portion 180j, the sandwiched portion 180k, and the sandwiched portion 180l are separated from each other. In the example shown in FIG. 4E, the front ends of the sandwiched portions 180j and 180k coincide with the imaginary line VL dividing the pump electrode 112 into two equal parts. In the example shown in FIG. 4E, the sandwiched portion 180 is disposed only in the rear end side region 112R of the pump electrode 112. Therefore, the layout shown in FIG. 4E belongs to type A.

FIG. 4F is a plan view showing the layout of the sandwiched portion.

Also in the example shown in FIG. 4F, the sandwiched portion 180 is located on each of both sides of the center line CL of the pump electrode 112. That is, also in the example shown in FIG. 4F, sandwiched portions 180m and 180n are located on both sides of the center line CL of the pump electrode 112. The longitudinal direction of the sandwiched portions 180m and 180n is a direction along the longitudinal direction of the pump electrode 112. In the example shown in FIG. 4F, the widths of the sandwiched portions 180m and 180n gradually increase from the front end side toward the rear end side. In the example shown in FIG. 4F, the sandwiched portions 180m and 180n each have a part having a curved shape. The curved portions of the sandwiched portions 180m and 180n are located on the center line CL side of the pump electrode 112. In the example shown in FIG. 4F, the distance between the sandwiched portion 180m and the sandwiched portion 180n decreases from the front end side toward the rear end side of the sensor element 12. In the example shown in FIG. 4F, the sandwiched portion 180 is disposed only in the rear end side region 112R of the pump electrode 112. Therefore, the layout shown in FIG. 4F belongs to type A.

Figure 6A:
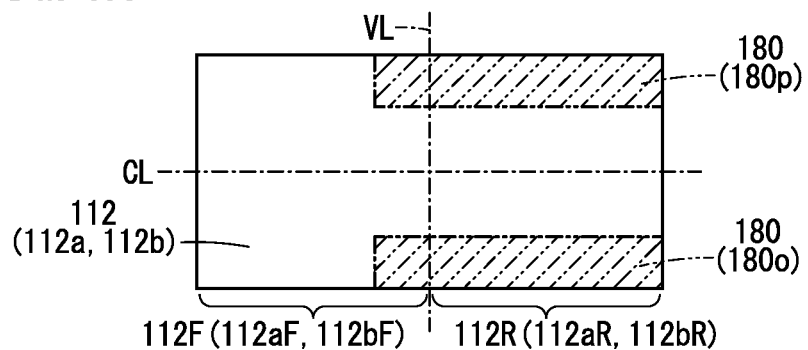
FIGS. 6A and 6B are plan views each showing an example of the layout of the sandwiched portion.

FIG. 6A is a plan view showing an example of the layout of the sandwiched portion.

In the example shown in FIG. 6A, the sandwiched portion 180 is located on each of both sides of the center line CL of the pump electrode 112. That is, in the example shown in FIG. 6A, sandwiched portions 180o and 180p are located on both sides of the center line CL of the pump electrode 112. The longitudinal direction of the sandwiched portions 180o and 180p is a direction along the longitudinal direction of the pump electrode 112. In the example shown in FIG. 6A, the front ends of the sandwiched portions 180o and 180p are located closer to the front end side than the imaginary line VL is, the imaginary line dividing the pump electrode 112 into two equal parts. In the example shown in FIG. 6A, the rear ends of the sandwiched portions 180o and 180p coincide with the rear end of the pump electrode 112. In the example shown in FIG. 6A, the sandwiched portions 180o and 180p disposed in the rear end side region 112R extend to a part of the front end side region 112F. A layout in which the sandwiched portions 180o and 180p disposed in the rear end side region 112R extend into the front end side region 112F is referred to as the layout of type B.

Figure 6B:
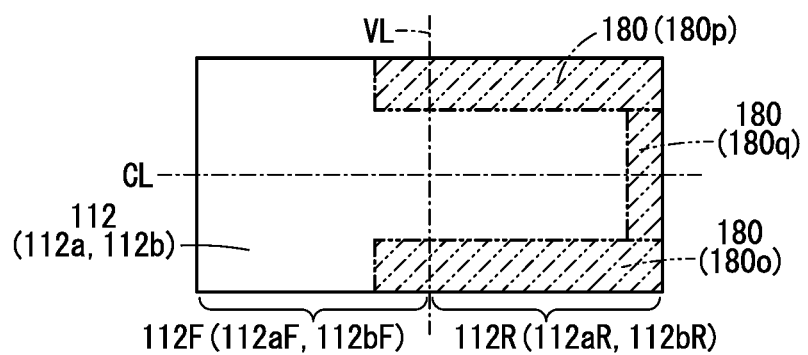

FIG. 6B is a plan view showing an example of the layout of the sandwiched portion.

In the example shown in FIG. 6B, the sandwiched portion 180 is disposed similarly to the example shown in FIG. 6A. That is, in the example shown in FIG. 6B, the sandwiched portions 180o and 180p are disposed similarly to the example shown in FIG. 6A. In the example shown in FIG. 6B, the sandwiched portion 180 is further located at the end portion of the pump electrode 112 on the rear end side. That is, in the example shown in FIG. 6B, a sandwiched portion 180q is further located at the end portion of the pump electrode 112 on the rear end side. The longitudinal direction of the sandwiched portion 180q is orthogonal to the longitudinal direction of the pump electrode 112. In the example shown in FIG. 6B, the front ends of the sandwiched portions 180o and 180p are located closer to the front end side than the imaginary line VL is, the imaginary line dividing the pump electrode 112 into two equal parts. In the example shown in FIG. 6B, the rear ends of the sandwiched portions 180o and 180p coincide with the rear end of the pump electrode 112. In the example shown in FIG. 6B, in plan view, both ends of the sandwiched portion 180q in the longitudinal direction reach the regions where the sandwiched portions 180o and 180p are disposed. In the example shown in FIG. 6B, the sandwiched portion 180 disposed in the rear end side region 112R extends into the front end side region 112F. That is, in the example shown in FIG. 6B, the sandwiched portions 180o and 180p disposed in the rear end side region 112R extend into the front end side region 112F. Therefore, the layout shown in FIG. 6B belongs to type B.

FIG. 7A is a plan view showing an example of the layout of the sandwiched portion.

In the example shown in FIG. 7A, the sandwiched portions 180a and 180b are disposed similarly to the example shown in FIG. 4A. In the example shown in FIG. 7A, the sandwiched portion 180 is further located at the end portion of the pump electrode 112 on the front end side. That is, in the example shown in FIG. 7A, a sandwiched portion 180r is further located at the end portion of the pump electrode 112 on the front end side. The longitudinal direction of the sandwiched portion 180r is orthogonal to the longitudinal direction of the pump electrode 112. The dimension of the sandwiched portion 180r in the direction orthogonal to the longitudinal direction of the pump electrode 112 is equal to the dimension of the pump electrode 112 in the direction orthogonal to the longitudinal direction of the pump electrode 112. In the example shown in FIG. 7A, the sandwiched portion 180r that is separate from the sandwiched portions 180a and 180b disposed in the rear end side region 112R is disposed in the front end side region 112F. A layout, in which the sandwiched portion 180r that is separate from the sandwiched portions 180a and 180b disposed in the rear end side region 112R is disposed in the front end side region 112F, is referred to as the layout of type C.

FIG. 7B is a plan view showing an example of the layout of the sandwiched portion.

In the example shown in FIG. 7B, the sandwiched portions 180a and 180b are disposed similarly to the example shown in FIG. 4A. In the example shown in FIG. 7B, the sandwiched portion 180 is further located at the end portion of the pump electrode 112 on the front end side. That is, in the example shown in FIG. 7B, sandwiched portions 180s and 180t are further located at the end portion of the pump electrode 112 on the front end side. More specifically, the sandwiched portions 180s and 180t are located at corner portions on both sides of the front end portion of the pump electrode 112. The sandwiched portions 180s and 180t each have a triangular planar shape. In the example shown in FIG. 7B, the widths of the sandwiched portions 180s and 180t gradually decrease from the front end side toward the rear end side. In the example shown in FIG. 7B, the distance between the sandwiched portion 180s and the sandwiched portion 180t increases from the front end side toward the rear end side. In the example shown in FIG. 7B, the front ends of the sandwiched portions 180a and 180b coincide with the imaginary line VL dividing the pump electrode 112 into two equal parts. In the example shown in FIG. 7B, the front ends of the sandwiched portions 180s and 180t coincide with the front end of the pump electrode 112. In the example shown in FIG. 7B, the sandwiched portions 180s and 180t that are separate from the sandwiched portions 180a and 180b disposed in the rear end side region 112R are disposed in the front end side region 112F. Therefore, the layout shown in FIG. 7B belongs to type C.

FIG. 7C is a plan view showing an example of the layout of the sandwiched portion.

In the example shown in FIG. 7C, the sandwiched portions 180a and 180b are disposed similarly to the example shown in FIG. 4A. In the example shown in FIG. 7C, the sandwiched portion 180 is further located at the end portion of the pump electrode 112 on the front end side. That is, in the example shown in FIG. 7C, a sandwiched portion 180u is further located at the end portion of the pump electrode 112 on the front end side. The longitudinal direction of the sandwiched portion 180u is orthogonal to the longitudinal direction of the pump electrode 112. The dimension of the sandwiched portion 180u in the direction orthogonal to the longitudinal direction of the pump electrode 112 is smaller than the dimension of the pump electrode 112 in the direction orthogonal to the longitudinal direction of the pump electrode 112. Both end portions of the sandwiched portion 180u in the longitudinal direction of the sandwiched portion 180u are located on the inner side of a side of the pump electrode 112 that extends in the longitudinal direction. In the example shown in FIG. 7C, the sandwiched portion 180u that is separate from the sandwiched portions 180a and 180b disposed in the rear end side region 112R is disposed in the front end side region 112F. Therefore, the layout shown in FIG. 7C belongs to type C.

FIG. 7D is a plan view showing an example of the layout of the sandwiched portion.

In the example shown in FIG. 7D, the sandwiched portions 180o and 180p are disposed similarly to the example shown in FIG. 6A. In the example shown in FIG. 7D, the sandwiched portion 180r is further located similarly to the example shown in FIG. 7A. In the example shown in FIG. 7D, the sandwiched portion 180r that is separate from the sandwiched portions 180o and 180p disposed in the rear end side region 112R is disposed in the front end side region 112F. Therefore, the layout shown in FIG. 7D belongs to type C.

Figure 8A:
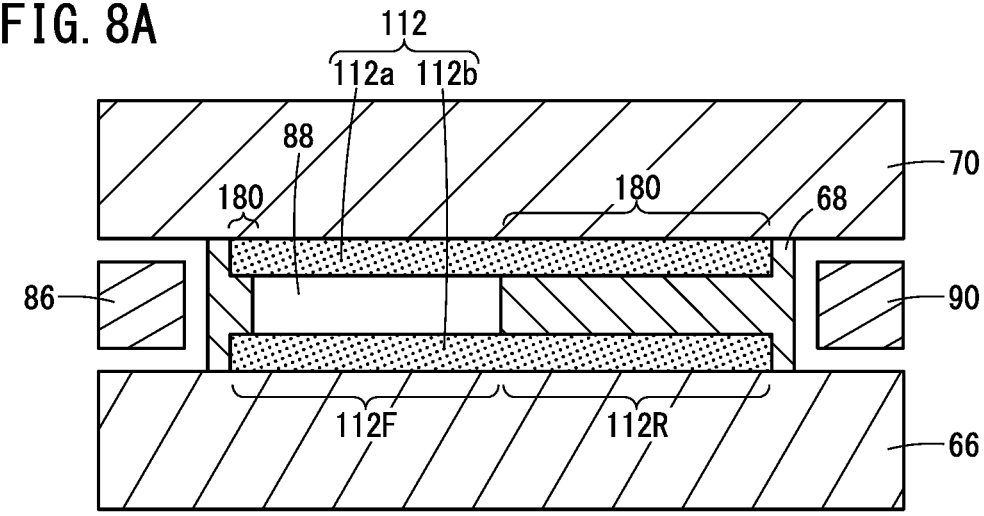
FIGS. 8A, 8B and 8C are cross-sectional views each showing an example of a part of the sensor element according to the embodiment.
Figure 8B:
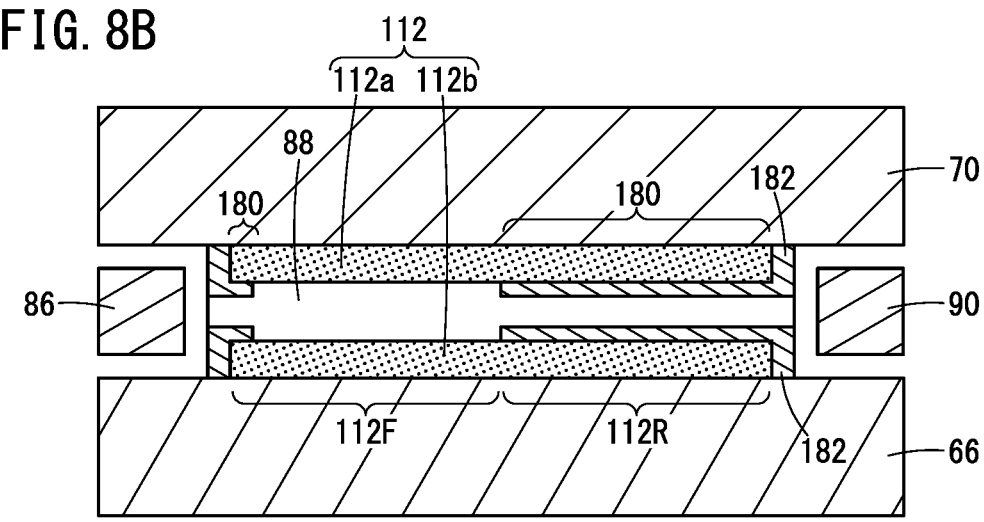
Figure 8C:
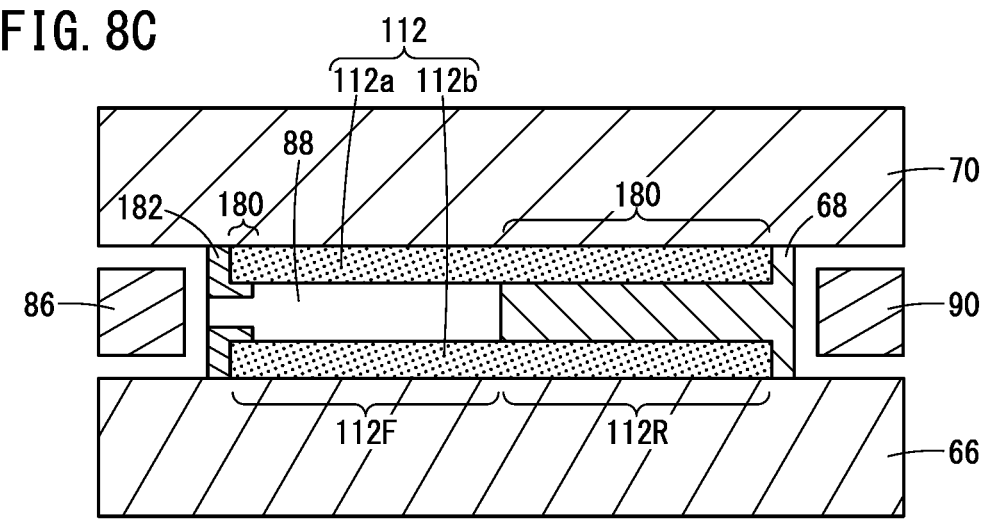

FIGS. 8A to 8C are cross-sectional views each showing a part of the sensor element according to the present embodiment. FIGS. 8A to 8C show cross sections along the longitudinal direction of the sensor element 12. FIGS. 8A to 8C correspond to the layouts shown in FIGS. 7A to 7D.

In the example shown in FIG. 8A, a part of the pump electrode 112 is sandwiched between the spacer layer 68 and the solid electrolyte layers 66 and 70 in both the sandwiched portion 180 located in the rear end side region 112R and the sandwiched portion 180 located in the front end side region 112F.

In the example shown in FIG. 8B, a part of the pump electrode 112 is covered with a part of the covering layer 182 in both the sandwiched portion 180 located in the rear end side region 112R and the sandwiched portion 180 located in the front end side region 112F.

In the example shown in FIG. 8C, a part of the pump electrode 112 is sandwiched between the spacer layer 68 and the solid electrolyte layers 66 and 70 in the sandwiched portion 180 located in the rear end side region 112R. On the other hand, in the sandwiched portion 180 located in the front end side region 112F, a part of the pump electrode 112 is covered with a part of the covering layer 182. In the sandwiched portion 180 located in the rear end side region 112R, a part of the pump electrode 112 may be covered with a part of the covering layer 182. A part of the pump electrode 112 may be sandwiched between the spacer layer 68 and the solid electrolyte layers 66 and 70 in the sandwiched portion 180 located in the front end side region 112F.

EXAMPLES

In Examples 1 to 16 and Comparative Examples 1 to 5, a peeling test for the pump electrode 112 and a pump performance test were performed. The test results are shown in FIGS. 9 and 10. FIGS. 9 and 10 are diagrams showing tables illustrating test results.

The peeling test for the pump electrode 112 was performed as follows. That is, the gas sensor 10 was placed in an air atmosphere at room temperature, and a test cycle including an ON state for 70 seconds and an OFF state for 50 seconds following the ON state was repeated 100,000 times. In the ON state, a predetermined voltage was applied to each part of the gas sensor 10. In the OFF state, no voltage was applied to each part of the gas sensor 10. In the ON state, power was supplied to the heater 164. In the ON state, signals were transmitted to and received from the gas sensor 10. In the off state, power supply to the heater 164 was stopped. In the OFF state, transmission and reception of signals to and from the gas sensor 10 were stopped. During the peeling test, the main pump cell 110 continued to operate. That is, the pump current Ip0 was kept at 15 μA. After the peeling test was completed, the pump electrode 112 was observed. When the pump electrode 112 was observed, X-ray CT was used. Further, when the pump electrode 112 was observed, the pump electrode 112 was cut as necessary.

The evaluation criteria of the result of the peeling test for the pump electrode 112 are as follows.

A: A 100% portion of the pump electrode 112 is maintained without peeling.

B: The area of the portion that is maintained without peeling is 50% or more of the area of the pump electrode 112.

C: The area of the portion that is maintained without peeling is less than 50% of the area of the pump electrode 112.

The evaluation criteria of the pump performance are as follows.

A: A sufficiently good pump performance is obtained.

B: A comparatively good pump performance is obtained.

C: The pump performance is not sufficiently obtained.

Example 1

In Example 1, the layout of the sandwiched portion 180 was Type A. That is, the sandwiched portion 180 was disposed only in the rear end side region 112R of the pump electrode 112. The total area of the pump electrode 112 was 7.1 mm$^2$. In Example 1, the area of the sandwiched portion 180 was 0.4 mm$^2$. That is, the area of the sandwiched portion 180 was set to be relatively small. In Example 1, the effective area of the pump electrode 112 was 6.7 mm$^2$. That is, in Example 1, the area of the portion which was exposed in the measured gas flow path 79, of the pump electrode 112 was 6.7 mm$^2$. The effective area of the front end side region 112F of the pump electrode 112 was 3.55 mm$^2$. That is, the area of the portion which was exposed in the measured gas flow path 79, of the front end side region 112F was 3.55 mm$^2$. The effective area of the rear end side region 112R of the pump electrode 112 was 3.15 mm$^2$. That is, the area of the portion which was exposed in the measured gas flow path 79, of the rear end side region 112R was 3.15 mm$^2$. The ratio of the area of the sandwiched portion 180 to the total area of the pump electrode 112 was 6%. The evaluation result of the peeling test for the pump electrode 112 was B. Further, the evaluation result of the pump performance test was A. A ratio Q of the effective area of the front end side region 112F to the effective area of the pump electrode 112 was 53.0%. That is, the area of the portion which was exposed in the measured gas flow path 79, of the front end side region 112F was larger than the area of the portion which was exposed in the measured gas flow path 79, of the rear end side region 112R.

Example 2

In Example 2, the layout of the sandwiched portion 180 was type A. That is, the sandwiched portion 180 was disposed only in the rear end side region 112R of the pump electrode 112. The total area of the pump electrode 112 was 7.4 mm$^2$. The area of the sandwiched portion 180 was 2.2 mm$^2$. That is, the area of the sandwiched portion 180 was set to be relatively large. The effective area of the pump electrode 112 was 5.2 mm$^2$. The effective area of the front end side region 112F of the pump electrode 112 was 3.70 mm$^2$. The effective area of the rear end side region 112R of the pump electrode 112 was 1.50 mm$^2$. The ratio of the area of the sandwiched portion 180 to the total area of the pump electrode 112 was 30%. The evaluation result of the peeling test for the pump electrode 112 was A. Further, the evaluation result of the pump performance test was B. The ratio Q of the effective area of the front end side region 112F to the effective area of the pump electrode 112 was 71.2%.

Example 3

In Example 3, the layout of the sandwiched portion 180 was type B. That is, the sandwiched portion 180 disposed in the rear end side region 112R was extended to a part of the front end side region 112F. The total area of the pump electrode 112 was 7.4 mm$^2$. In Example 3, the area of the sandwiched portion 180 was 0.7 mm$^2$. That is, the area of the sandwiched portion 180 was set to be relatively small. In Example 3, the effective area of the pump electrode 112 was 6.7 mm$^2$. The effective area of the front end side region 112F of the pump electrode 112 was 3.60 mm$^2$. The effective area of the rear end side region 112R of the pump electrode 112 was 3.10 mm$^2$. The ratio of the area of the sandwiched portion 180 to the total area of the pump electrode 112 was 9%. The evaluation result of the peeling test for the pump electrode 112 was B. Further, the evaluation result of the pump performance test was A. The ratio Q of the effective area of the front end side region 112F to the effective area of the pump electrode 112 was 53.7%.

Example 4

In Example 4, the layout of the sandwiched portion 180 was type B. That is, the sandwiched portion 180 disposed in the rear end side region 112R was extended to a part of the front end side region 112F. The total area of the pump electrode 112 was 7.3 mm$^2$. In Example 4, the area of the sandwiched portion 180 was 3.2 mm$^2$. That is, the area of the sandwiched portion 180 was set to be relatively large. The effective area of the pump electrode 112 was 4.1 mm$^2$. The effective area of the front end side region 112F of the pump electrode 112 was 2.45 mm$^2$. The effective area of the rear end side region 112R of the pump electrode 112 was 1.65 mm$^2$. The ratio of the area of the sandwiched portion 180 to the total area of the pump electrode 112 was 44%. The evaluation result of the peeling test for the pump electrode 112 was A. Further, the evaluation result of the pump performance test was B. The ratio Q of the effective area of the front end side region 112F to the effective area of the pump electrode 112 was 59.8%.

Example 5

In Example 5, the layout of the sandwiched portion 180 was type B. That is, the sandwiched portion 180 disposed in the rear end side region 112R was extended to a part of the front end side region 112F. The total area of the pump electrode 112 was 7.5 mm$^2$. The area of the sandwiched portion 180 was 1.2 mm$^2$. The effective area of the pump electrode 112 was 6.3 mm$^2$. That is, the area of the portion which was exposed in the measured gas flow path 79, of the pump electrode 112, was 6.3 mm$^2$. The effective area of the front end side region 112F of the pump electrode 112 was 3.35 mm$^2$. The effective area of the rear end side region 112R of the pump electrode 112 was 2.95 mm$^2$. The ratio of the area of the sandwiched portion 180 to the total area of the pump electrode 112 was 16%. The evaluation result of the peeling test for the pump electrode 112 was A. Further, the evaluation result of the pump performance test was A. The ratio Q of the effective area of the front end side region 112F to the effective area of the pump electrode 112 was 53.2%.

Example 6

In Example 6, the layout of the sandwiched portion 180 was type B. That is, the sandwiched portion 180 disposed in the rear end side region 112R was extended to a part of the front end side region 112F. The total area of the pump electrode 112 was 7.5 mm$^2$. In Example 6, the area of the sandwiched portion 180 was 3.4 mm$^2$. The effective area of the pump electrode 112 was 4.1 mm$^2$. The effective area of the front end side region 112F of the pump electrode 112 was 2.55 mm$^2$. The effective area of the rear end side region 112R of the pump electrode 112 was 1.55 mm$^2$. The ratio of the area of the sandwiched portion 180 to the total area of the pump electrode 112 was 45%. The evaluation result of the peeling test for the pump electrode 112 was A. Further, in Example 6, the evaluation result of the pump performance test was B. In Example 6, the ratio Q of the effective area of the front end side region 112F to the effective area of the pump electrode 112 was 62.2%.

Example 7

In Example 7, the layout of the sandwiched portion 180 was type B. That is, the sandwiched portion 180 disposed in the rear end side region 112R was extended to a part of the front end side region 112F. The total area of the pump electrode 112 was 9.0 mm$^2$. The area of the sandwiched portion 180 was 1.4 mm$^2$. The effective area of the pump electrode 112 was 7.6 mm$^2$. The effective area of the front end side region 112F of the pump electrode 112 was 4.10 mm$^2$. The effective area of the rear end side region 112R of the pump electrode 112 was 3.50 mm$^2$. The ratio of the area of the sandwiched portion 180 to the total area of the pump electrode 112 was 16%. The evaluation result of the peeling test for the pump electrode 112 was A. Further, in Example 7, the evaluation result of the pump performance test was A. In Example 7, the ratio Q of the effective area of the front end side region 112F to the effective area of the pump electrode 112 was 53.9%.

Example 8

In Example 8, the layout of the sandwiched portion 180 was type B. That is, the sandwiched portion 180 disposed in the rear end side region 112R was extended to a part of the front end side region 112F. The total area of the pump electrode 112 was 9.9 mm$^2$. In Example 8, the area of the sandwiched portion 180 was 1.4 mm$^2$. The effective area of the pump electrode 112 was 8.5 mm$^2$. The effective area of the front end side region 112F of the pump electrode 112 was 4.45 mm$^2$. The effective area of the rear end side region 112R of the pump electrode 112 was 4.05 mm$^2$. In Example 8, the ratio of the area of the sandwiched portion 180 to the total area of the pump electrode 112 was 14%. In Example 8, the evaluation result of the peeling test for the pump electrode 112 was A. Further, in Example 8, the evaluation result of the pump performance test was A. In Example 8, the ratio Q of the effective area of the front end side region 112F to the effective area of the pump electrode 112 was 52.4%.

Example 9

In Example 9, the layout of the sandwiched portion 180 was type B. That is, the sandwiched portion 180 disposed in the rear end side region 112R was extended to a part of the front end side region 112F. The total area of the pump electrode 112 was 10.6 mm². The area of the sandwiched portion 180 was 1.5 mm². The effective area of the pump electrode 112 was 9.1 mm². The effective area of the front end side region 112F of the pump electrode 112 was 4.70 mm². The effective area of the rear end side region 112R of the pump electrode 112 was 4.40 mm². The ratio of the area of the sandwiched portion 180 to the total area of the pump electrode 112 was 14%. The evaluation result of the peeling test for the pump electrode 112 was A. Further, in Example 9, the evaluation result of the pump performance test was A. In Example 9, the ratio Q of the effective area of the front end side region 112F to the effective area of the pump electrode 112 was 51.6%.

Example 10

In Example 10, the layout of the sandwiched portion 180 was type B. That is, the sandwiched portion 180 disposed in the rear end side region 112R was extended to a part of the front end side region 112F. The total area of the pump electrode 112 was 12.3 mm². The area of the sandwiched portion 180 was 1.8 mm². The effective area of the pump electrode 112 was 10.5 mm². The effective area of the front end side region 112F of the pump electrode 112 was 5.75 mm². The effective area of the rear end side region 112R of the pump electrode 112 was 4.75 mm². The ratio of the area of the sandwiched portion 180 to the total area of the pump electrode 112 was 15%. The evaluation result of the peeling test for the pump electrode 112 was A. Further, in Example 10, the evaluation result of the pump performance test was A. The ratio Q of the effective area of the front end side region 112F to the effective area of the pump electrode 112 was 54.8%.

Example 11

In Example 11, the layout of the sandwiched portion 180 was type B. That is, the sandwiched portion 180 disposed in the rear end side region 112R was extended to a part of the front end side region 112F. The total area of the pump electrode 112 was 15.0 mm². The area of the sandwiched portion 180 was 4.0 mm². The effective area of the pump electrode 112 was 11.0 mm². The effective area of the front end side region 112F of the pump electrode 112 was 6.50 mm². The effective area of the rear end side region 112R of the pump electrode 112 was 4.50 mm². The ratio of the area of the sandwiched portion 180 to the total area of the pump electrode 112 was 27%. The evaluation result of the peeling test for the pump electrode 112 was A. Further, in Example 11, the evaluation result of the pump performance test was A. In Example 11, the ratio Q of the effective area of the front end side region 112F to the effective area of the pump electrode 112 was 59.1%.

Example 12

In Example 12, the layout of the sandwiched portion 180 was type B. That is, the sandwiched portion 180 disposed in the rear end side region 112R was extended to a part of the front end side region 112F. The total area of the pump electrode 112 was 15.0 mm². The area of the sandwiched portion 180 was 7.4 mm². The effective area of the pump electrode 112 was 7.6 mm². The effective area of the front end side region 112F of the pump electrode 112 was 5.00 mm². The effective area of the rear end side region 112R of the pump electrode 112 was 2.60 mm². The ratio of the area of the sandwiched portion 180 to the total area of the pump electrode 112 was 49%. The evaluation result of the peeling test for the pump electrode 112 was A. Further, the evaluation result of the pump performance test was A. The ratio Q of the effective area of the front end side region 112F to the effective area of the pump electrode 112 was 65.8%.

Example 13

In Example 13, the layout of the sandwiched portion 180 was type B. More specifically, the layout corresponds to that of FIG. 6B. That is, the sandwiched portion 180 disposed in the rear end side region 112R was extended to a part of the front end side region 112F, and the sandwiched portion 180 was further located at the end portion of the pump electrode 112 on the rear end side. The total area of the pump electrode 112 was 9.9 mm². The area of the sandwiched portion 180 was 2.0 mm². In Example 13, the effective area of the pump electrode 112 was 7.9 mm². The effective area of the front end side region 112F of the pump electrode 112 was 4.25 mm². The effective area of the rear end side region 112R of the pump electrode 112 was 3.65 mm². The ratio of the area of the sandwiched portion 180 to the total area of the pump electrode 112 was 20%. The evaluation result of the peeling test for the pump electrode 112 was A. Further, in Example 13, the evaluation result of the pump performance test was A. In Example 13, the ratio Q of the effective area of the front end side region 112F to the effective area of the pump electrode 112 was 53.8%.

Example 14

In Example 14, the layout of the sandwiched portion 180 was type C. That is, the sandwiched portion 180 that is separate from the sandwiched portion 180 disposed in the rear end side region 112R was disposed in the front end side region 112F. The total area of the pump electrode 112 was 9.5 mm². The area of the sandwiched portion 180 was 2.3 mm². The effective area of the pump electrode 112 was 7.2 mm². The effective area of the front end side region 112F of the pump electrode 112 was 3.69 mm². The effective area of the rear end side region 112R of the pump electrode 112 was 3.50 mm². The ratio of the area of the sandwiched portion 180 to the total area of the pump electrode 112 was 24%. The evaluation result of the peeling test for the pump electrode 112 was A. Further, in Example 14, the evaluation result of the pump performance test was A. The ratio Q of the effective area of the front end side region 112F to the effective area of the pump electrode 112 was 51.3%.

Example 15

In Example 15, the layout of the sandwiched portion 180 was type C. That is, the sandwiched portion 180 that is separate from the sandwiched portion 180 disposed in the rear end side region 112R was disposed in the front end side region 112F. The total area of the pump electrode 112 was 9.8 mm². The area of the sandwiched portion 180 was 2.4 mm². The effective area of the pump electrode 112 was 7.4 mm². The effective area of the front end side region 112F of the pump electrode 112 was 3.80 mm². The effective area of the rear end side region 112R of the pump electrode 112 was 3.60 mm². The ratio of the area of the sandwiched portion 180 to the total area of the pump electrode 112 was 24%. The evaluation result of the peeling test for the pump electrode 112 was A. Further, in Example 15, the evaluation result of the pump performance test was A. The ratio Q of the effective area of the front end side region 112F to the effective area of the pump electrode 112 was 51.4%.

Example 16

In Example 16, the layout of the sandwiched portion 180 was type C. That is, the sandwiched portion 180 that is separate from the sandwiched portion 180 disposed in the rear end side region 112R was disposed in the front end side region 112F. The total area of the pump electrode 112 was 9.9 mm$^2$. The area of the sandwiched portion 180 was 2.9 mm$^2$. The effective area of the pump electrode 112 was 7.0 mm$^2$. The effective area of the front end side region 112F of the pump electrode 112 was 3.95 mm$^2$. The effective area of the rear end side region 112R of the pump electrode 112 was 3.05 mm$^2$. The ratio of the area of the sandwiched portion 180 to the total area of the pump electrode 112 was 29%. The evaluation result of the peeling test for the pump electrode 112 was A. Further, in Example 16, the evaluation result of the pump performance test was A. The ratio Q of the effective area of the front end side region 112F to the effective area of the pump electrode 112 was 56.4%.

Comparative Example 1

In Comparative Example 1, the total area of the pump electrode 112 was 7.5 mm$^2$. The area of the sandwiched portion 180 was 0 mm$^2$. That is, the sandwiched portion 180 was not provided. The effective area of the pump electrode 112 was 7.5 mm$^2$. The effective area of the front end side region 112F of the pump electrode 112 was 3.75 mm$^2$. The effective area of the rear end side region 112R of the pump electrode 112 was 3.75 mm$^2$. The ratio of the area of the sandwiched portion 180 to the total area of the pump electrode 112 was 0%. The evaluation result of the peeling test for the pump electrode 112 was C. The evaluation result of the pump performance test was A. The ratio Q of the effective area of the front end side region 112F to the effective area of the pump electrode 112 was 50.0%.

Comparative Example 2

In Comparative Example 2, the total area of the pump electrode 112 was 9.9 mm$^2$. The area of the sandwiched portion 180 was 0 mm$^2$. That is, the sandwiched portion 180 was not provided. The effective area of the pump electrode 112 was 9.9 mm$^2$. The effective area of the front end side region 112F of the pump electrode 112 was 4.95 mm$^2$. The effective area of the rear end side region 112R of the pump electrode 112 was 4.95 mm$^2$. The ratio of the area of the sandwiched portion 180 to the total area of the pump electrode 112 was 0%. The evaluation result of the peeling test for the pump electrode 112 was C. Further, in Comparative Example 2, the evaluation result of the pump performance test was A. In Comparative Example 2, the ratio Q of the effective area of the front end side region 112F to the effective area of the pump electrode 112 was 50.0%.

Comparative Example 3

In Comparative Example 3, the total area of the pump electrode 112 was 12.3 mm$^2$. The area of the sandwiched portion 180 was 0 mm$^2$. That is, the sandwiched portion 180 was not provided. The effective area of the pump electrode 112 was 12.3 mm$^2$. The effective area of the front end side region 112F of the pump electrode 112 was 6.15 mm$^2$. The effective area of the rear end side region 112R of the pump electrode 112 was 6.15 mm$^2$. The ratio of the area of the sandwiched portion 180 to the total area of the pump electrode 112 was 0%. The evaluation result of the peeling test for the pump electrode 112 was C. Further, in Comparative Example 3, the evaluation result of the pump performance test was A. In Comparative Example 3, the ratio Q of the effective area of the front end side region 112F to the effective area of the pump electrode 112 was 50.0%.

Comparative Example 4

In Comparative Example 4, the total area of the pump electrode 112 was 9.8 mm$^2$. The area of the sandwiched portion 180 was 6.5 mm$^2$. That is, the area of the sandwiched portion 180 was set to be excessively large. The sandwiched portion 180 was disposed on the entire peripheral edge portion of the pump electrode 112. The effective area of the pump electrode 112 was 3.3 mm$^2$. The effective area of the front end side region 112F of the pump electrode 112 was 1.65 mm$^2$. The effective area of the rear end side region 112R of the pump electrode 112 was 1.65 mm$^2$. The ratio of the area of the sandwiched portion 180 to the total area of the pump electrode 112 was 66%. The evaluation result of the peeling test for the pump electrode 112 was B. Cracks occurred in the pump electrode 112 due to a difference in thermal expansion coefficient between the pump electrode 112 and the solid electrolyte layers 66 and 70 and the like. Further, the evaluation result of the pump performance test was C. The ratio Q of the effective area of the front end side region 112F to the effective area of the pump electrode 112 was 50.0%.

Comparative Example 5

In Comparative Example 5, the total area of the pump electrode 112 was 9.8 mm$^2$. The area of the sandwiched portion 180 was 6.5 mm$^2$. That is, the area of the sandwiched portion 180 was set to be excessively large. The sandwiched portion 180 was disposed on the entire peripheral edge portion of the pump electrode 112. The effective area of the pump electrode 112 was 3.3 mm$^2$. The effective area of the front end side region 112F of the pump electrode 112 was 1.60 mm$^2$. The effective area of the rear end side region 112R of the pump electrode 112 was 1.70 mm$^2$. That is, by setting the area of the sandwiched portion 180 in the front end side region 112F to be relatively large, the effective area of the front end side region 112F of the pump electrode 112 was set to be relatively small. The ratio of the area of the sandwiched portion 180 to the total area of the pump electrode 112 was 66%. The evaluation result of the peeling test for the pump electrode 112 was B. Cracks occurred in the pump electrode 112 due to a difference in thermal expansion coefficient between the pump electrode 112 and the solid electrolyte layers 66 and 70 and the like. Further, the evaluation result of the pump performance test was C. In Comparative Example 5, the ratio Q of the effective area of the front end side region 112F to the effective area of the pump electrode 112 was 48.5%.

In this way, by setting the ratio of the area of the sandwiched portion 180 to the total area of the pump electrode 112 within the range of 5% to 50%, it is possible to prevent peeling of the pump electrode 112. In addition, by setting the ratio of the area of the sandwiched portion 180 to the total area of the pump electrode 112 within the range of 10% to 50%, it is possible to more reliably prevent peeling of the pump electrode 112.

In addition, by setting the effective area of the pump electrode 112 to 4.0 mm² or more, good pump performance can be obtained.

As described above, according to the present embodiment, at least a part of the pump electrode 112 is sandwiched between the spacer layer 68 and the solid electrolyte layers 66 and 70, or is covered with the covering layer 182 formed on the inner surface of the measured gas flow path 79. Therefore, the pump electrode 112 can be prevented from peeling off. In addition, since the area of the portion which is exposed in the measured gas flow path 79, of the pump electrode 112 is 4 mm² or more, good pump performance can be ensured. In addition, according to the present embodiment, the area of the portion which is exposed in the measured gas flow path 79, of the front end side region 112F is larger than the area of the portion which is exposed in the measured gas flow path 79, of the rear end side region 112R. Therefore, a large exposed area of the pump electrode 112 can be ensured in a region having a higher oxygen concentration. Ensuring a large exposed area of the pump electrode 112 in a region having a higher oxygen concentration contributes to ensuring a sufficient pump performance and contributes to accurate operation of the sensor element 12. As described above, according to the present embodiment, it is possible to provide the gas sensor 10 capable of suppressing peeling of the pump electrode 112 while ensuring good performance.

[Modification]

Although the preferred embodiment of the present invention has been described above, the present invention is not limited to the above-described embodiment, and various modifications can be made thereto without departing from the scope of the present invention.

Figure 11:
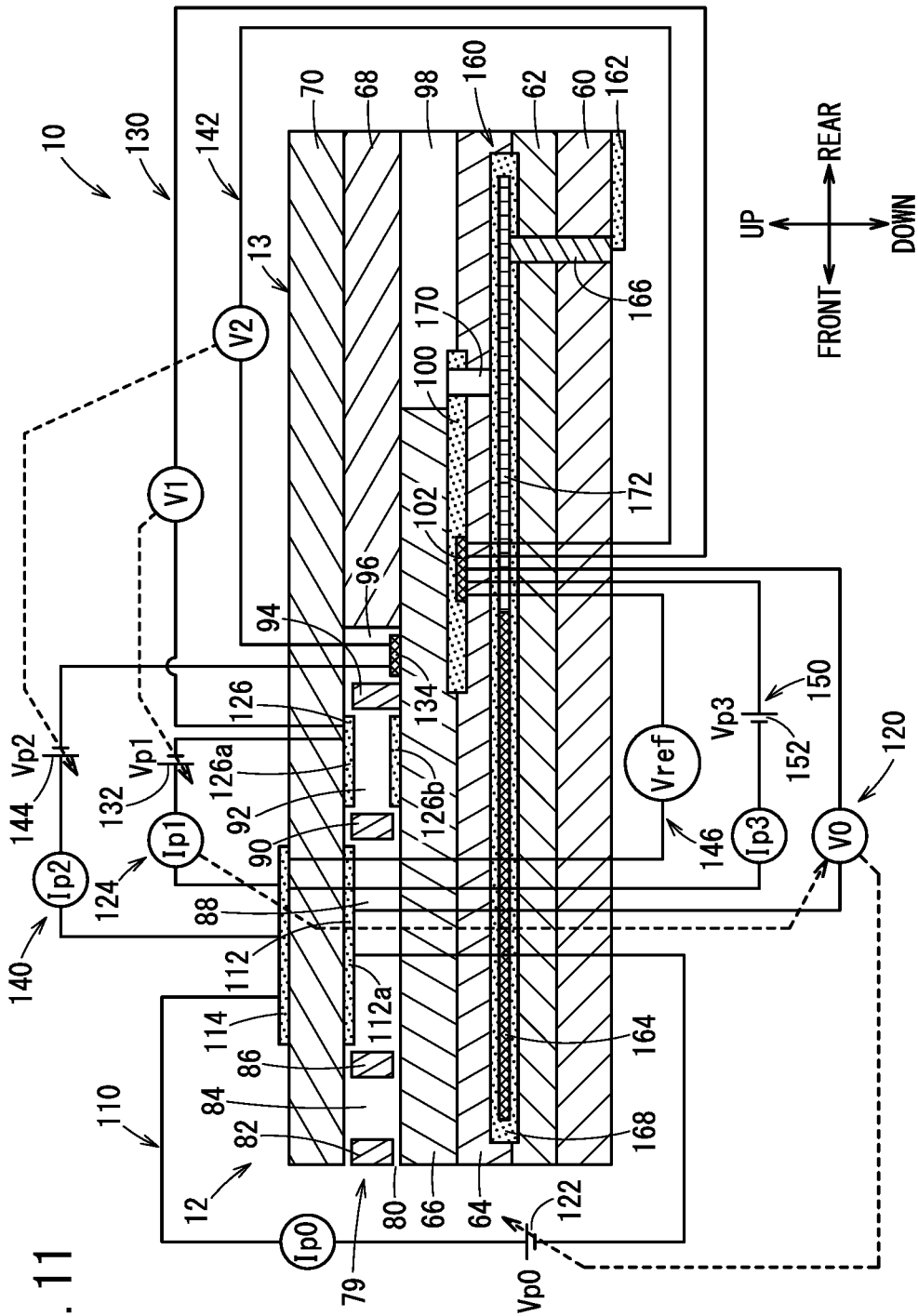
FIG. 11 is a cross-sectional view showing a part of a gas sensor according to a modification.

For example, in the above-described embodiment, the case where the pump electrode 112 is constituted by the top pump electrode 112a and the bottom pump electrode 112b has been described as an example, but the present invention is not limited thereto. For example, the pump electrode 112 may be constituted only by the top pump electrode 112a. FIG. 11 is a cross-sectional view showing a part of a gas sensor according to a modification. In the example shown in FIG. 11, the pump electrode 112 is constituted only by the top pump electrode 112a. In addition, the pump electrode 112 may be constituted only by the bottom pump electrode 112b.

In the above-described embodiment, the case where the fourth diffusion control portion 94 is provided between the second internal cavity 92 and the third internal cavity 96 has been described as an example, but the present invention is not limited thereto. The fourth diffusion control portion 94 may not be provided between the second internal cavity 92 and the third internal cavity 96. In this case, the second internal cavity 92 and the third internal cavity 96 may be integrated with each other. In this case, the auxiliary pump electrode 126 and the measurement electrode 134 are located in the same internal cavity.

The embodiments described above can be summarized as follows.

A gas sensor (10) comprises: a laminate (13) comprising a plurality of layers including at least one layer made of a solid electrolyte; a measured gas flow path (79) which is formed in the laminate and through which a measured gas introduced through a gas inlet (80) flows, the gas inlet being located on a front end side that is one side in a longitudinal direction of the laminate; and a pump electrode (112) formed along a longitudinal direction of the measured gas flow path and exposed in the measured gas flow path. The pump electrode includes a front end side region (112F) located closer to the front end side than a center of the pump electrode is, and a rear end side region (112R) located on a rear end side that is an opposite side of the center of the pump electrode from the front end side. In a part of the rear end side region, the pump electrode is sandwiched between, among the plurality of layers, a first layer (66, 70) and a second layer (68) adjacent to the first layer, or is covered with a covering layer (182) formed on an inner surface of the measured gas flow path. An area of a portion which is exposed in the measured gas flow path, of the pump electrode is 4 mm² or more. An area of a portion which is exposed in the measured gas flow path, of the front end side region is larger than an area of a portion which is exposed in the measured gas flow path, of the rear end side region. According to such a configuration, since at least a part of the pump electrode is sandwiched between the first layer and the second layer, or is covered with the covering layer formed on the inner surface of the measured gas flow path, it is possible to suppress peeling of the pump electrode. In addition, since the area of the portion which is exposed in the measured gas flow path, of the pump electrode is 4 mm² or more, it is possible to ensure good pump performance. Further, according to such a configuration, the area of the portion which is exposed in the measured gas flow path, of the front end side region is larger than the area of the portion which is exposed in the measured gas flow path, of the rear end side region. Therefore, a large exposed area of the pump electrode can be ensured in a region having a higher oxygen concentration. Ensuring a large exposed area of the pump electrode in a region having a higher oxygen concentration contributes to ensuring a sufficient pump performance and contributes to accurate operation of the sensor element. As described above, according to such a configuration, it is possible to provide a gas sensor capable of suppressing peeling of the pump electrode while ensuring good performance.

The laminate may further include a third layer (70) adjacent to the second layer, the measured gas flow path may be formed in the second layer, a bottom surface and a top surface of the measured gas flow path may be defined by the first layer (66) and the third layer, respectively, a side surface of the measured gas flow path may be defined by the second layer, the pump electrode may include a bottom pump electrode (112b) formed on the bottom surface of the measured gas flow path, and a top pump electrode (112a) formed on the top surface of the measured gas flow path, in a part of the rear end side region, one of the bottom pump electrode and the top pump electrode may be sandwiched between the first layer and the second layer, or may be covered with a covering layer formed on the inner surface of the measured gas flow path, and in a part of the rear end side region, another of the bottom pump electrode and the top pump electrode may be sandwiched between the second layer and the third layer, or may be covered with a covering layer formed on the inner surface of the measured gas flow path.

A ratio of an area of a portion which is not exposed in the measured gas flow path, of the pump electrode to a total area of the pump electrode may be 5% to 50%. According to such a configuration, it is possible to suppress peeling of the pump electrode while preventing cracks from occurring in the pump electrode.

The ratio of the area of the portion which is not exposed in the measured gas flow path, of the pump electrode to the total area of the pump electrode may be 10% to 50%. According to such a configuration, it is possible to more reliably suppress peeling of the pump electrode while preventing cracks from occurring in the pump electrode.

A planar shape of the pump electrode may be rectangular, and a portion which is sandwiched between the first layer and the second layer, of the pump electrode or a portion which is covered with the covering layer, of the pump electrode may be located at least on each of both sides of a center line (CL) of the pump electrode, the center line extending along the longitudinal direction of the measured gas flow path. According to such a configuration, it is possible to contribute to suppression of peeling of the pump electrode.

In at least a part of the front end side region, the pump electrode may be further sandwiched between the first layer and the second layer, or may be further covered with a covering layer formed on the inner surface of the measured gas flow path. According to such a configuration, peeling of the pump electrode can be more reliably suppressed.

An end portion of the pump electrode on the front end side may be further sandwiched between the first layer and the second layer, or may be further covered with a covering layer formed on the inner surface of the measured gas flow path. According to such a configuration, peeling of the pump electrode can be more reliably suppressed.

An end portion of the pump electrode on the rear end side may be further sandwiched between the first layer and the second layer, or may be further covered with a covering layer formed on the inner surface of the measured gas flow path. According to such a configuration, peeling of the pump electrode can be more reliably suppressed.

The first layer and the second layer may be made of a solid electrolyte.

The first layer may be made of a solid electrolyte, and the second layer may be made of an insulator.

The third layer may be made of a solid electrolyte.

What is claimed is:

1. A gas sensor comprising:
   a laminate comprising a plurality of layers including at least one layer made of a solid electrolyte;
   a measured gas flow path which is formed in the laminate and through which a measured gas introduced through a gas inlet flows, the gas inlet being located on a front end side that is one side in a longitudinal direction of the laminate; and
   a pump electrode formed along a longitudinal direction of the measured gas flow path and exposed in the measured gas flow path, wherein
   the pump electrode includes a front end side region located closer to the front end side than a center of the pump electrode is, and a rear end side region located on a rear end side that is an opposite side of the center of the pump electrode from the front end side,
   in a part of the rear end side region, the pump electrode is covered with a covering layer formed on an inner surface of the measured gas flow path,
   a portion of the pump electrode, which is not covered with the covering layer, is an effective area of the pump electrode,
   the effective area of the pump electrode is 4 mm$^2$ or more,
   an area of a portion of the front end side region, which is exposed in the measured gas flow path, is larger than an area of a portion of the rear end side region, which is exposed in the measured gas flow path,
   the laminate includes, among the plurality of layers, a first layer, a second layer adjacent to the first layer, and a third layer adjacent to the second layer, the measured gas flow path is formed in the second layer,
   a bottom surface and a top surface of the measured gas flow path are defined by the first layer and the third layer, respectively,
   a side surface of the measured gas flow path is defined by the second layer,
   a maximum thickness of the covering layer is less than a thickness of the second layer,
   a sandwiched portion in the pump electrode as a portion covered with the covering layer includes a first sandwiched portion on one side of a center line extending in a longitudinal direction of the pump electrode and a second sandwiched portion on the other side of the center line,
   a longitudinal direction of the first sandwiched portion and a longitudinal direction of the second sandwiched portion are directions along the longitudinal direction of the pump electrode, and
   a distance between the first sandwiched portion and the second sandwiched portion gradually decreases from the front end side to the rear end side.

2. The gas sensor according to claim 1, further comprising:
   a plurality of covering layers formed on the inner surface of the measured gas flow path, wherein
   the pump electrode includes a bottom pump electrode formed on the bottom surface of the measured gas flow path, and a top pump electrode formed on the top surface of the measured gas flow path,
   in the part of the rear end side region, one of the bottom pump electrode and the top pump electrode is covered with a first covering layer of the plurality of covering layers,
   in the part of the rear end side region, another of the bottom pump electrode and the top pump electrode is covered with a second covering layer of the plurality of covering layers formed on the inner surface of the measured gas flow path, and
   a sum of a maximum thickness of the first covering layer and a maximum thickness of the second covering layer is less than the thickness of the second layer.

3. The gas sensor according to claim 1, wherein
   a ratio of an area of a portion of the pump electrode, which is not exposed in the measured gas flow path, to a total area of the pump electrode is 5% to 50%.

4. The gas sensor according to claim 3, wherein
   the ratio of the area of the portion of the pump electrode, which is not exposed in the measured gas flow path, to the total area of the pump electrode is 10% to 50%.

5. The gas sensor according to claim 1, wherein
   a planar shape of the pump electrode is rectangular.

6. The gas sensor according to claim 1, wherein
   at least two of the plurality of layers are each made of a solid electrolyte.

7. The gas sensor according to claim 1, wherein
   at least one layer of the plurality of layers is made of an insulator.

8. A gas sensor comprising:
   a laminate comprising a plurality of layers including at least one layer made of a solid electrolyte;
   a measured gas flow path which is formed in the laminate and through which a measured gas introduced through a gas inlet flows, the gas inlet being located on a front end side that is one side in a longitudinal direction of the laminate; and
   a pump electrode formed along a longitudinal direction of the measured gas flow path and exposed in the measured gas flow path, wherein the pump electrode includes a front end side region located closer to the front end side than a center of the pump electrode is, and a rear end side region located on a rear end side that is an opposite side of the center of the pump electrode from the front end side, in a part of the rear end side region, the pump electrode is covered with a covering layer formed on an inner surface of the measured gas flow path, at least a portion of the pump electrode, which is not covered with the covering layer, is an effective area of the pump electrode, the effective area of the pump electrode is 4 mm$^2$ or more, an area of a portion of the front end side region, which is exposed in the measured gas flow path, is larger than an area of a portion of the rear end side region, which is exposed in the measured gas flow path, the laminate includes, among the plurality of layers, a first layer, a second layer adjacent to the first layer, and a third layer adjacent to the second layer, the measured gas flow path is formed in the second layer, a bottom surface and a top surface of the measured gas flow path are defined by the first layer and the third layer, respectively, a side surface of the measured gas flow path is defined by the second layer, a maximum thickness of the covering layer is less than a thickness of the second layer, a sandwiched portion in the pump electrode as a portion covered with the covering layer includes a first sandwiched portion, a second sandwiched portion, a third sandwiched portion, and a fourth sandwiched portion, a longitudinal direction of the first sandwiched portion and a longitudinal direction of the second sandwiched portion are directions along a longitudinal direction of the pump electrode, the first sandwiched portion is positioned in the rear end side region on one side of a center line extending in the longitudinal direction of the pump electrode, the second sandwiched portion is positioned in the rear end side region on the other side of the center line, the third sandwiched portion is positioned at an end of the front end side on the one side of the center line, the fourth sandwiched portion is positioned at an end of the front end side on the other side of the center line, and a distance between the third sandwiched portion and the fourth sandwiched portion gradually increases from the front end side to the rear end side.

9. A gas sensor comprising:

a laminate comprising a plurality of layers including at least one layer made of a solid electrolyte;

a measured gas flow path which is formed in the laminate and through which a measured gas introduced through a gas inlet flows, the gas inlet being located on a front end side that is one side in a longitudinal direction of the laminate; and a pump electrode formed along a longitudinal direction of the measured gas flow path and exposed in the measured gas flow path, wherein the pump electrode includes a front end side region located closer to the front end side than a center of the pump electrode is, and a rear end side region located on a rear end side that is an opposite side of the center of the pump electrode from the front end side, in a part of the rear end side region, the pump electrode is covered with a covering layer formed on an inner surface of the measured gas flow path, at least a portion of the pump electrode, which is not covered with the covering layer, is an effective area of the pump electrode, the effective area of the pump electrode is 4 mm$^2$ or more, an area of a portion of the front end side region, which is exposed in the measured gas flow path, is larger than an area of a portion of the rear end side region, which is exposed in the measured gas flow path, the laminate includes, among the plurality of layers, a first layer, a second layer adjacent to the first layer, and a third layer adjacent to the second layer, the measured gas flow path is formed in the second layer, a bottom surface and a top surface of the measured gas flow path are defined by the first layer and the third layer, respectively, a side surface of the measured gas flow path is defined by the second layer, a maximum thickness of the covering layer is less than a thickness of the second layer, a sandwiched portion in the pump electrode as a portion covered with the covering layer includes a first sandwiched portion, a second sandwiched portion, and a third sandwiched portion, a longitudinal direction of the first sandwiched portion and a longitudinal direction of the second sandwiched portion are directions along a longitudinal direction of the pump electrode, a longitudinal direction of the third sandwiched portion is a direction perpendicular to the longitudinal direction of the pump electrode, the first sandwiched portion is positioned in the rear end side region on one side of a center line extending in the longitudinal direction of the pump electrode, the second sandwiched portion is positioned in the rear end side region on the other side of the center line, the third sandwiched portion is positioned at an end of the front end side, a size of the third sandwiched portion in the direction perpendicular to the longitudinal direction of the pump electrode is smaller than a size of the pump electrode in the direction perpendicular to the longitudinal direction of the pump electrode, and the third sandwiched portion is spaced from the first sandwiched portion and from the second sandwiched portion.

* * * * *